US011433234B2

(12) United States Patent
Rigaux

(10) Patent No.: US 11,433,234 B2
(45) Date of Patent: *Sep. 6, 2022

(54) EXTERNAL TRIGEMINAL NERVE STIMULATION FOR THE ACUTE NON-INVASIVE TREATMENT OF MIGRAINE ATTACKS

(71) Applicant: CEFALY Technology sprl, Seraing (BE)

(72) Inventor: Pierre Rigaux, Liège (BE)

(73) Assignee: Cefaly Technology SPRL

( * ) Notice: Subject to any disclaimer, the term of this patent is extended or adjusted under 35 U.S.C. 154(b) by 177 days.

This patent is subject to a terminal disclaimer.

(21) Appl. No.: 16/614,397

(22) PCT Filed: May 16, 2018

(86) PCT No.: PCT/EP2018/062779
§ 371 (c)(1),
(2) Date: Nov. 18, 2019

(87) PCT Pub. No.: WO2018/210949
PCT Pub. Date: Nov. 22, 2018

(65) Prior Publication Data
US 2020/0179689 A1    Jun. 11, 2020

(30) Foreign Application Priority Data
May 19, 2017   (EP) .................................. 17171961

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0492* (2013.01);
(Continued)

(58) Field of Classification Search
CPC ............ A61N 1/36075; A61N 1/36034; A61N 1/0492; A61N 1/0456; A61N 1/36021
See application file for complete search history.

(56) References Cited

U.S. PATENT DOCUMENTS

| 2,782,786 A | 2/1957 | Krasno |
| 3,620,219 A | 11/1971 | Barker |

(Continued)

FOREIGN PATENT DOCUMENTS

| CA | 2082092 A1 | 5/1993 |
| CA | 915 928 A | 12/2014 |

(Continued)

OTHER PUBLICATIONS

"Migraine", International Classification of Headache Disorders, 3rd edition, 2013, 3 pages.

(Continued)

*Primary Examiner* — Alyssa M Alter
(74) *Attorney, Agent, or Firm* — Cooley LLP

(57) ABSTRACT

The current invention concerns a system and a method for the acute non-invasive treatment of a migraine attack. The system comprises at least one skin electrode for placement on the forehead of a patient. The system is configured for providing consecutive biphasic electrical pulses via said at least one skin electrode to the supratrochlear and supraorbital nerves of the ophthalmic branch of the trigeminal nerve during a prolonged time span. Preferably, the time span is at least 10 minutes.

19 Claims, 7 Drawing Sheets

(52) U.S. Cl.
CPC ....... *A61N 1/0496* (2013.01); *A61N 1/36034* (2017.08); *A61N 1/36025* (2013.01)

(56) References Cited

U.S. PATENT DOCUMENTS

| | | | |
|---|---|---|---|
| 3,709,228 | A | 1/1973 | Barker |
| 3,746,004 | A | 7/1973 | Elson |
| 3,971,387 | A | 7/1976 | Mantell |
| 3,998,213 | A | 12/1976 | Price |
| 4,112,941 | A | 9/1978 | Larimore |
| 4,165,750 | A | 8/1979 | Aleev |
| 4,209,234 | A | 6/1980 | McCooeye |
| 4,288,222 | A | 9/1981 | Kling |
| 4,509,521 | A | 4/1985 | Barry |
| 4,537,198 | A | 8/1985 | Corbett |
| 4,816,964 | A | 3/1989 | Weiss |
| 4,841,954 | A | 6/1989 | Kalsi |
| 4,957,480 | A | 9/1990 | MoreninQs |
| 5,496,363 | A | 3/1996 | BurQio |
| 5,527,357 | A | 6/1996 | Springer, Jr. |
| 5,540,734 | A | 7/1996 | Zabara |
| 5,726,916 | A | 3/1998 | Smyth |
| 5,785,040 | A | 7/1998 | Axelgaard |
| 5,913,836 | A | 6/1999 | Groux |
| 6,077,237 | A | 6/2000 | Campbell |
| 6,198,955 | B1 | 3/2001 | Axelgaard |
| 6,233,472 | B1 | 5/2001 | Bennett |
| 6,563,424 | B1 | 5/2003 | Kaario |
| 6,654,626 | B2 | 11/2003 | Devlin |
| 6,735,475 | B1 | 5/2004 | Whitehurst |
| 6,954,668 | B1 | 10/2005 | Cuozzo |
| 7,949,403 | B2 | 5/2011 | Palermo |
| 8,380,315 | B2 | 2/2013 | DeGiorgio |
| 8,428,734 | B2 | 4/2013 | Rigaux et al. |
| 8,583,238 | B1 | 11/2013 | Heldman et al. |
| 8,615,309 | B2 | 12/2013 | Craig |
| 8,702,584 | B2 | 4/2014 | Rigaux et al. |
| 8,805,548 | B2 | 8/2014 | Mignolet et al. |
| 9,042,991 | B2 | 5/2015 | Reed |
| 9,108,041 | B2 | 8/2015 | Craig |
| 9,233,244 | B2 | 1/2016 | Pal |
| 9,238,139 | B2 | 1/2016 | Degiorgio |
| 9,364,674 | B2 | 6/2016 | Cook |
| 9,433,774 | B2 | 9/2016 | Dar et al. |
| 9,504,827 | B2 | 11/2016 | Degiorgio |
| 9,675,794 | B2 | 5/2017 | Miller |
| 9,682,236 | B2 | 6/2017 | Degiorgio |
| 9,731,127 | B2 | 8/2017 | Kealey |
| 9,782,584 | B2 | 10/2017 | Cartledge et al. |
| 9,872,979 | B2 | 1/2018 | Dar et al. |
| 9,956,405 | B2 | 5/2018 | Goldwasser et al. |
| 9,987,486 | B2 | 6/2018 | Rigaux |
| 10,016,601 | B2 | 7/2018 | Cook |
| 10,058,704 | B2 | 8/2018 | Degiorgio |
| 10,195,455 | B2 | 2/2019 | Stubbeman |
| 10,322,283 | B2 | 6/2019 | Degiorgio |
| 10,376,695 | B2 | 8/2019 | Errico |
| 10,376,965 | B2 | 8/2019 | Hengsberger et al. |
| 10,485,970 | B2 | 11/2019 | Gerber |
| 10,525,254 | B2 | 1/2020 | Miller |
| 10,537,729 | B2 | 1/2020 | Cook |
| 10,576,279 | B2 | 3/2020 | Muller |
| 10,773,080 | B2 * | 9/2020 | Rigaux ............. A61N 1/36034 |
| 10,864,371 | B2 | 12/2020 | Shimada |
| 11,052,251 | B2 | 7/2021 | Muller |
| 11,065,444 | B2 | 7/2021 | Errico |
| 2002/0161416 | A1 | 10/2002 | Huang |
| 2003/0045922 | A1 | 3/2003 | Northrop |
| 2004/0039328 | A1 | 2/2004 | Henley |
| 2004/0073129 | A1 | 4/2004 | Caldwel |
| 2004/0260359 | A1 | 12/2004 | Osrud |
| 2005/0038486 | A1 | 2/2005 | Mulholland |
| 2005/0187497 | A1 | 8/2005 | Nguyen |
| 2006/0077340 | A1 | 4/2006 | Curiel |
| 2006/0136009 | A1 | 6/2006 | Staffel |
| 2006/0154078 | A1 | 7/2006 | Watanabe |
| 2006/0293608 | A1 | 12/2006 | Rothman |
| 2007/0233194 | A1 | 10/2007 | Craig |
| 2007/0276449 | A1 | 11/2007 | Gunter |
| 2007/0276451 | A1 | 11/2007 | Rigaux |
| 2008/0051764 | A1 | 2/2008 | Dent |
| 2009/0082831 | A1 | 3/2009 | Paul |
| 2009/0105576 | A1 | 4/2009 | Do |
| 2009/0112282 | A1 | 4/2009 | Kast |
| 2009/0210028 | A1 | 8/2009 | Rigaux |
| 2010/0030299 | A1 | 2/2010 | Covalin |
| 2010/0113959 | A1 | 5/2010 | Pascual-Leone |
| 2010/0274327 | A1 | 10/2010 | Carroll |
| 2010/0306902 | A1 | 12/2010 | Bourque |
| 2011/0282129 | A1 | 11/2011 | Rigaux |
| 2011/0319975 | A1 | 12/2011 | Ho |
| 2013/0282095 | A1 | 10/2013 | Mignolet |
| 2013/0296967 | A1 | 11/2013 | Skaribas et al. |
| 2014/0081369 | A1 | 3/2014 | Sosa et al. |
| 2014/0188200 | A1 | 7/2014 | DeGiorgio et al. |
| 2014/0228906 | A1 | 8/2014 | DeGiorgio et al. |
| 2014/0324146 | A1 | 10/2014 | Muller |
| 2015/0066104 | A1 | 3/2015 | Wingeier |
| 2015/0335888 | A1 | 11/2015 | Demers |
| 2016/0022987 | A1 | 1/2016 | Zschaeck |
| 2017/0165485 | A1 | 6/2017 | Sullivan et al. |
| 2017/0281940 | A1 | 10/2017 | de Oliveira et al. |
| 2018/0014740 | A1 | 1/2018 | Hayakawa |
| 2018/0056059 | A1 | 3/2018 | Rigaux |
| 2018/0056065 | A1 | 3/2018 | Muller |
| 2018/0333576 | A1 | 11/2018 | Rigaux |
| 2020/0046970 | A1 | 2/2020 | Gerber |
| 2020/0054887 | A1 | 2/2020 | Levin |
| 2020/0147340 | A1 | 5/2020 | Tyler |
| 2020/0298001 | A1 | 9/2020 | Muller |
| 2021/0370047 | A1 | 12/2021 | Rigaux |

FOREIGN PATENT DOCUMENTS

| | | |
|---|---|---|
| CN | 2531817 Y | 1/2003 |
| CN | 103269746 B | 8/2010 |
| CN | 102698360 A | 10/2012 |
| CN | 206239894 U | 6/2017 |
| DE | 102007021960 A1 | 11/2008 |
| EP | 2646109 B1 | 10/2013 |
| EP | 3639883 A1 | 4/2020 |
| JP | H 9-294815 A | 11/1997 |
| JP | 009-531154 A | 9/2009 |
| JP | 2011-509743 A | 3/2011 |
| JP | 2012-509121 A | 4/2012 |
| JP | 2013-506534 A | 2/2013 |
| KR | 10-2014-0037803 | 3/2014 |
| KR | 10-1473443 B1 | 12/2014 |
| WO | WO 00/45701 A1 | 8/2000 |
| WO | WO 00/71075 A8 | 11/2000 |
| WO | WO 01/03638 A1 | 1/2001 |
| WO | WO 2006/051370 A1 | 5/2006 |
| WO | WO 2006/063417 A1 | 6/2006 |
| WO | WO 2008/004204 A1 | 1/2008 |
| WO | WO 2008/005478 A2 | 1/2008 |
| WO | WO 09/091578 A1 | 7/2009 |
| WO | WO 2009/137683 A2 | 11/2009 |
| WO | WO 2010/057998 A1 | 5/2010 |
| WO | WO-2011/044173 A1 | 4/2011 |
| WO | WO 2011/151742 A1 | 12/2011 |
| WO | WO 2012/079778 A1 | 6/2012 |
| WO | WO 2013/022840 A1 | 2/2013 |
| WO | WO 2013/104552 A1 | 7/2013 |
| WO | WO 2013/152316 A1 | 10/2013 |
| WO | WO 2014/141213 A1 | 9/2014 |
| WO | WO 2016/044659 A1 | 3/2016 |
| WO | 2016/106182 A1 | 6/2016 |
| WO | 2016155773 A1 | 10/2016 |
| WO | WO 2016/042278 A1 | 3/2018 |
| WO | 2018/210949 A1 | 11/2018 |
| WO | WO 2020/079218 A1 | 4/2020 |

(56) References Cited

OTHER PUBLICATIONS

Cady et al. (2015) "A Randomized, Double-Blind, Placebo-Controlled Study of Breath Powered Nasal Delivery of Sumatriptan Powder (AVP-825) in the Treatment of Acute Migraine (The TARGET Study)", Headache, 55(1):88-100.
Dameron et al. (2015) "Triptans in the Acute Treatment of Migraine: A Systematic Review and Network Meta-Analysis", Headache, 4:221-235.
Farkkila et al. (2012) "Efficacy and Tolerability of Lasmiditan, An Oral 5-HT1F Receptor Agonist, for the Acute Treatment of Migraine: A Phase 2 Randomised, Placebo-Controlled, Parallel-Group, Dose-Ranging Study", The Lancet Neurology, 11(5):405-413.
Goldstein et al. (2012) "A Sumatriptan Iontophoretic Transdermal System for the Acute Treatment of Migraine", Headache, 52(9):1402-1410.
Lipton et al. (2010) "Single-Pulse Transcranial Magnetic Stimulation for Acute Treatment of Migraine with Aura: A Randomised, Double-Blind, Parallel-Group, Sham-Controlled Trial", The Lancet Neurology, 9(4):373-380.
Spierings et al. (2018) "Randomized, Double-Blind, Placebocontrolled, Parallel-Group, Multi-Center Study of the Safety and Efficacy of Adam Zolmitriptan for the Acute Treatment of Migraine", Cephalalgia, 38(2):215-224.
Straube et al. (2015) "Treatment of Chronic Migraine with Transcutaneous Stimulation of the Auricular Branch of the Vagal Nerve (Auricular T-VNS): A Randomized, Monocentric Clinical Trial", The Journal of Headache and Pain, 16:63.
The Diclofenac-K/Sumatriptan Migraine Study Group "Acute Treatment of Migraine Attacks: Efficacy and Safety of a Nonsteroidal Anti-inflammatory Drug, Diclofenac-potassium, in Comparison to Oral Sumatriptan and Placebo", Cephalalgia, 19(4):232-240.
Voss et al. (2016) "A Phase IIb Randomized, Double-blind, Placebo-controlled Trial of Ubrogepant for the Acute Treatment of Migraine", Cephalalgia, 36(9):887-898.
Clark et al., "Long-Term Pain Reduction Does Not Imply Improved functional Outcome in Patients Treated with Combined Supraorbital and Occipital Nerve Stimulation for Chronic Migraine", Nueomodulation: Technology at the Neural Interface, 2016.
Gaul et al., "Non-Invasive Vagus Nerve Stimulation for Prevention and Acute Treatment of Chronic Cluster Headache (PREVA): A Randomised Controlled Study", Cephalalgia, 2015.
Giani et al., "P062. Sensory Modalities During Dreams in Migraine", The Journal of Headache and Pain, 2015.
Jasper et al., "Implanted Occipital Nerve Stimulators", Pain Physician, 2008.
Magis et al., "Safety and Patients' Satisfaction of Transcutaneous Supraorbital NeuroStimulation (tSNS) with the Cefaly Device in Headache Treatment: A Survey of 2,313 headache sufferers in the General Population", The Journal of Headache and Pain, 2013.
Magis et al., "Occipital Nerve Stimulation for Drug-Resistant Chronic Cluster Headache: A Prospective Pilot Study", Lancet Neurol, 2007.
Piquet et al., "Supraorbital Transcutaneous Neurostimulation Has Sedative Effects in Health Subjects", BMC Neurology, 2011.
Reed et al., "Combined Occipital and Supraorbital Neurostimulation for the Treatment of Chronic Migraine Headaches: Initial Experience", Cephalalgia, 2009.
Russo et al., "Transcutaneous Supraorbital Neurostimulation in "de novo" Patients With Migraine Without Aura: the First Italian Experience", The Journal of Headache and Pain, 2015.
Saper et al., "Occipital Nerve Stimulation for the Treatment of Intractable Chronic Migraine Headache: ONSTIM Feasibility Study", Cephalalgia, 2010.
Schoenen et al., "Stimulation of the Sphenopalatine Ganglion (SPG) for Cluster Headache Treatment. Pathway CH-I: A Randomized, Sham-Controlled Study", Cephalalgia, 2013.
Schoenen et al., "Migraine Prevention with a Supraorbital Transcutaneous Stimulator: A Randomized Controlled Trial", Neurology, Feb. 6, 2013.
Silberstein et al., "Chronic Migraine Headache Prevention with Noninvasive Vagus Nerve Stimulation", American Academy of Neurology, 2016.
Burton, Scaffolding to build a rational vaccine design strategy, PNAS, Oct. 19, 2010, pp. 17859-17860, vol. 107, No. 42.
Chou, et al., Acute migraine therapy with external trigeminal neurostimulation (ACME): A randomized controlled trial, Cephalalgia, 2019, pp. 3-14, vol. 39, No. 1.
Chou, et al., External Trigeminal Nerve Stimulation for the Acute Treatment of Migraine: Open-Label Trial on Safety and Efficacy, Neuromodulation, 2017 Oct. 2017, pp. 678-683, vol. 20, No. 7.
Cunningham, et al., Comparison of a Structural and a Functional Epitope, J. Mol. Biol., 1993, pp. 554-563, vol. 234.
Difore, et al., Transcutaneous supraorbital neurostimulation for the prevention of chronic migraine: a prospective, open-label preliminary trial, Neurological Sciences, 2017, pp. 201-206, vol. 38, No. S1.
Gori, et al., Peptides for immunological purposes: design, strategies and applications, Amino Acids, 2013, pp. 257-268, vol. 45.
He, et al., Approaching rational epitope vaccine design for hepatitis C virus with meta-server and multivalent scaffolding, Nature, Scientific Reports, Aug. 4, 2015, 16 pages.
Huang, et al., Mimotope-Based Prediction of B-Cell Epitopes, Immunoinformatics, Methods in Molecular Biology, Chapter 13, pp. 237-243, vol. 1184.
Kelley, et al., Thermodynamic Analysis of an Antibody Functional Epitope, Biochemistry, 1993, pp. 6828-6835, vol. 32.
Kozminsky, Transcutaneous Supraorbital Nerve Stimulation as a Rescue Therapy, Headache 2014; 54(Suppl 1): 12-12. (poster abstr).
Kuruvilla, et al., Acute treatment of migraine with external trigeminal nerve stimulation: A pilot trial, Cephalalgia Reports, 2019, pp. 1-6, vol. 2.
Lauristen, et al., Rationale for electrical parameter determination in external trigeminal nerve stimulation (eTNS) for migraine: A narrative review, Cephalalgia, 2019, pp. 750-760, vol. 39, No. 6.
Liljeroos, et al., Structural and Computational Biology in the Design of Immunogenic Vaccine Antigens, Journal of Immunology Research, Article ID 156241, 17 pages, vol. 2015.
Luo, et al., Targeting Melanoma Cells with Human High Molecular Weight-Melanoma Associated Antigen-Specific Antibodies Elicited by a Peptide Mimotope: Functional Effects, The Journal of Immunology, 2006, pp. 6046-6054.
Magis et al., Cerebral metabolism before and after external trigeminal nerve stimulation in episodic migraine, Cephalalgia, 2017, pp. 881-891, vol. 37, No. 9.
McLellan, et al., Design and Characterization of Epitope-Scaffold Immunogens That Present the Motavizumab Epitope from Respiratory Syncytial Virus, Journal of Molecular Biology, 2011, pp. 853-866, vol. 409.
Ohtaki, et al., Structure-Based Peptide Mimicry of Tumor-Associated Antigens, Monoclonal Antibodies in Immunodiagnosis and Immunotherapy, 2013, 5 pages, vol. 32, No. 1.
Pantophlet, et al., Immunofocusing: Antigen Engineering to Promote the Induction of HIV-Neutralizing Antibodies, TRENDS in Molecular Medicine, Nov. 2003, pp. 468-473, vol. 9 No. 11.
Penning, et al., A survey on migraine attack treatment with the CEFALY® device in regular users, Acta Neurologica Belgica, 2017, pp. 547-549, vol. 117, No. 2.
Pierce, et al., Structure-Based Design of Hepatitis C Virus Vaccines That Elicit Neutralizing Antibody Responses to a Conserved Epitope, Journal of Virology, Oct. 2017, 16 pages, vol. 91, No. 20.
Riemer, Mimotope vaccines: Epitope Mimics Induce Anti-cancer Antibodies, Immunol Letters, Oct. 31, 2007, 9 pages, vol. 113, No. 1.
Ru, et al., MimoDB: a New Repository for Mimotope Data Derived from Phage Display Technology, Molecules, 2010, pp. 8279-8288, vol. 15.
Schoenen et al., Efficacy and mode of action of external trigeminal neurostimulation in migraine, Expert Review of Neurotherapeutics, 2018, pp. 545-555, vol. 18, No. 7.
Tice, et al., Controversies in Migraine Management: A Technology Assessment Final Report Aug. 19, 2014, Completed by Institute for Clinical and Economic Review, Retrieved from: chrome-extension://

(56) References Cited

OTHER PUBLICATIONS efaidnbmnnnibpcajpcglclefindmkaj/viewer.html?pdfurl=https%3A%2F%2Ficer.org%2Fwp-content%2Fuploads%2F2020%2F10%2FCTAF_Migraine_Final_Report_081914-2.pdf&clen=1139085&chunk=true.

Vikelis, et al., Clinical experience with transcutaneous supraorbital nerve stimulation in patients with refractory migraine or with migraine and intolerance to topiramate: a prospective exploratory clinical study, BMC Neurol, May 2017, pp. 1-7, vol. 17, No. 1.

Wikipedia, Mimotope, 2 pages. Retrieved from: https://en.wikipedia.org/w/index.php?title=Mimotope&oldid=775942536.

Ahmed et al., Use of the percutaneous electrical nerve stimulation (PENS) in the short-term management of headache, Headache, 2000, pp. 311-315, vol. 40.

Allais et al., Non-pharmacological approaches to chronic headaches: transcutaneous electrical nerve stimulation, lasertherapy and acupuncture in transformed migraine treatment, Neurol Sci, 2003, pp. SI38-SI42, vol. 24.

Alon, Chapter 3—Principles of Electrical Stimulation, Clinical Electrotherapy Appleton & Lange, 1987, pp. 29-47.

Angelakis et al., Transcranial Direct Current Stimulation Effects in Disorders of Consciousness, Archives of Physical Medicine and Rehabilitation, 2014, pp. 283-289, vol. 95.

Bigland-Ritchie, EMG and Fatigue of Human Voluntary and Stimulated Contractions, Human Muscle Fatigue: Physiological Mechanisms, Pitman Medical London 1981 (Ciba Foundation Symposium 82), pp. 130-156.

European Patent Office, International Preliminary Report on Patentability for PCT/EP2011/054072, dated Jan. 16, 2013, 6 pages.

European Patent Office, International Preliminary Report on Patentability for PCT/EP2015/056889, dated Jun. 27, 2017, 14 pages.

European Patent Office, International Preliminary Report on Patentability for PCT/EP2018/062779, dated Jul. 22, 2019, 14 pages.

European Patent Office, International Preliminary Report on Patentability for PCT/IB2017/054905, dated Nov. 5, 2018, 17 pages.

European Patent Office, International Search Report and Written Opinion for for PCT/EP2011/054072, dated Jul. 27, 2011, 13 pages.

European Patent Office, International Search Report and Written Opinion for PCT/EP2018/062779, dated Jun. 15, 2018, 9 pages.

European Patent Office, International Search Report and Written Opinion for for PCT/EP2019/078355, dated Jan. 30, 2020, 12 pages.

European Patent Office, International Search Report and Written Opinion for for PCT/IB2017/054905, dated Nov. 7, 2017, 13 pages.

Farina et al., Headache and cervical spine disorders: Classification and treatment with transcutaneous electrical nerve stimulation, 1986, 3 pages.

International Bureau of WIPO, International Preliminary Report on Patentability for PCT/EP2019/078355, dated Apr. 14, 2021, 8 pages.

International Preliminary Examination Authority, English translation of International Preliminary Report on Patentability for PCT/BE2005/000135, dated Jun. 14, 2007, 9 pages.

International Preliminary Examination Authority, English translation of International Preliminary Report on Patentability for PCT/EP2013/050047, dated Jul. 13, 2014, 11 pages.

Jones et al., Excitation Frequency and Muscle Fatigue: Mechanical Responses during Voluntary and Stimulated Contractions, Experimental Neurology 64, 1979, pp. 401-413.

Jones, High and Low-Frequency Fatigue Revisited, Acta Physiol. Scand. 156, 1996, pp. 265-270.

Jones, Muscle Fatigue due to Changes Beyond the Neuromuscular Junction, Human Muscle Fatigue: Physiological Mechanisms, Pitman Medical London, 1981 (Ciba Foundation Symposium 82), pp. 178-196.

Levine et al., Relaxation of Spasticity by Electrical Stimulation of Antagonist Muscles, Arch. Phys. Med., 1952, pp. 668-673, vol. 33.

Melzack et al., Pain mechanisms: A new theory, Science, 1965, pp. 971-979, vol. 150.

Riederer, et al., Transcutaneous Supraorbilal Nerve Stimulation {l-SNS) with the Cefaly Device for Migraine Prevention: A Review of the Available Data, Pain and Therapy, Oct. 14, 2015, pp. pp. 135-147, vol. 4, No. 2.

Robinson et al., Clinical Electrophysiology, Instrumentation for Neuromuscular electrical stimulation, Lippincott Williams & Wilkins, 1989, 8 pages.

Solomon et al., Treatment of headache by transcutaneous electrical stimulation, Headache, 1985, pp. 12-15, vol. 25.

United States Patent and Trademark Office, Non-Final Office Action for U.S. Appl. No. 11/667,223, filed Jun. 11, 2009.

United States Patent and Trademark Office, Final Office Action for U.S. Appl. No. 11/667,223, filed Jun. 10, 2010.

United States Patent and Trademark Office, Non-Final Office Action for U.S. Appl. No. 11/667,223, filed Feb. 17, 2011.

United States Patent and Trademark Office, Non-Final Office Action for U.S. Appl. No. 11/667,223, filed Jul. 22, 2011.

United States Patent and Trademark Office, Non-Final Office Action for U.S. Appl. No. 11/667,223, filed Feb. 14, 2012.

United States Patent and Trademark Office, Final Office Action for U.S. Appl. No. 11/667,223, filed Aug. 3, 2012.

United States Patent and Trademark Office, Non-Final Office Action for U.S. Appl. No. 11/667,223, filed Apr. 30, 2013.

United States Patent and Trademark Office, Non-Final Office Action for U.S. Appl. No. 11/667,223, filed Apr. 24, 2014.

United States Patent and Trademark Office, Final Office Action for U.S. Appl. No. 11/667,223, filed Nov. 21, 2013.

United States Patent and Trademark Office, Notice of Allowance for U.S. Appl. No. 11/667,223, filed Aug. 26, 2014.

United States Patent and Trademark Office, Non-Final Office Action for U.S. Appl. No. 12/359,716, filed Sep. 13, 2011.

United States Patent and Trademark Office, Final Office Action for U.S. Appl. No. 12/359,716, filed Jul. 18, 2012.

United States Patent and Trademark Office, Notice of Allowance for U.S. Appl. No. 12/359,716, filed Jan. 2, 2013.

United States Patent and Trademark Office, Non-Final Office Action for U.S. Appl. No. 13/101,495, filed Mar. 29, 2013.

United States Patent and Trademark Office, Final Office Action for U.S. Appl. No. 13/101,495, filed Sep. 30, 2013.

United States Patent and Trademark Office, Notice of Allowance for U.S. Appl. No. 13/101,495, filed Dec. 10, 2013.

United States Patent and Trademark Office, Non-Final Office Action for U.S. Appl. No. 15/250,431, filed Nov. 22, 2017.

United States Patent and Trademark Office, Notice of Allowance for U.S. Appl. No. 15/250,431, filed Mar. 29, 2018.

United States Patent and Trademark Office, Restriction Requirment for U.S. Appl. No. 15/558,386, filed May 1, 2019.

United States Patent and Trademark Office, Non-Final Office Action for U.S. Appl. No. 15/558,386, filed May 31, 2019.

United States Patent and Trademark Office, Notice of Allowance for U.S. Appl. No. 15/558,386, filed Oct. 30, 2019.

United States Patent and Trademark Office, Non-Final Office Action for U.S. Appl. No. 15/980,220, filed Nov. 26, 2019.

United States Patent and Trademark Office, Notice of Allowance for U.S. Appl. No. 15/980,220, filed May 12, 2020.

United States Patent and Trademark Office, Non-Final Office Action for U.S. Appl. No. 16/803,481, filed Nov. 12, 2020.

United States Patent and Trademark Office, Notice of Allowance for U.S. Appl. No. 16/803,481, filed Mar. 10, 2021.

United States Patent and Trademark Office, Non-Final Office Action for U.S. Appl. No. 13/914,096, filed Dec. 16, 2013.

United States Patent and Trademark Office, Notice of Allowance for U.S. Appl. No. 13/914,096, filed Apr. 17, 2014.

United States Patent and Trademark Office, Non-Final Office Action for U.S. Appl. No. 14/328,396, filed Apr. 10, 2015.

Wal, Modulation of Spasticity: Prolonged Suppression of a Spinal Reflex by Electrical Stimulation, Science, Apr. 9, 1982, pp. 203-204, vol. 216.

Wall et al., Temporary abolition of pain in man, Science, Jan. 6, 1967, pp. 108-109.

(56) References Cited

OTHER PUBLICATIONS

Woolf et al., Antinociceptiv effect of peripheral segmental electrical stimulation in the rat, Pain, 1980, pp. 237-252, vol. 8.

* cited by examiner

EXTERNAL TRIGEMINAL NERVE STIMULATION FOR THE ACUTE NON-INVASIVE TREATMENT OF MIGRAINE ATTACKS

This application claims the benefit of European Application No. 17171961.0 filed May 19, 2017 and PCT/EP2018/062779 filed May 16, 2018, International Publication No. WO2018/210949 A1, which are hereby incorporated by reference in their entirety as if fully set forth herein.

TECHNICAL FIELD

The current invention concerns a system and a method for the acute non-invasive treatment of a migraine attack. The system comprises at least one skin electrode for placement on the forehead of a patient. The system is configured for providing consecutive biphasic electrical pulses via said at least one skin electrode to the supratrochlear and supraorbital nerves of the ophthalmic branch of the trigeminal nerve during a prolonged time span.

BACKGROUND

Migraine is a common neurobiological disorder characterized by recurrent episodes of headache accompanied by sensory hypersensitivity, which can significantly impair quality of life. Acute treatments are used during a migraine attack with the objective to abort or reduce headache pain and restore normal function, while preventive treatments are intended to reduce attack frequency and severity.

Current acute migraine treatments are primarily pharmacologic approaches, with the most commonly used medications being analgesics, non-steroidal anti-inflammatory drugs (NSAIDs) and triptans. These drugs bear several contraindications and are associated with moderate to severe side effects. In patients with frequent and/or prolonged migraine attacks, excessive consumption of acute migraine drugs may lead to headache chronification and medication overuse headache, which portends a worse outcome. Moreover, some patients (particularly those with chronic migraine) may become resistant to conventional migraine medications and thus do not achieve sufficient pain relief. Medication-related adverse effects and limited effectiveness highlight the need for non-pharmacologic therapies.

Recent studies suggest that neurostimulation may be a promising modality for the treatment of headache disorders. Several neuromodulation technics have been investigated for the treatment of primary headaches. Pain Physician 11(2), 187-200 (2008) discloses open trials wherein percutaneous occipital nerve stimulation (p-ONS) was effective for chronic migraine. Lancet Neurology 6(4), 314-321 (2007) discloses the effectiveness of p-ONS for chronic cluster headache. Cephalalgia 31(3), 271-285 (2011) discloses positive results for p-ONS in a controlled study for chronic migraine. Cephalalgia 30(3), 260-271 (2010) discloses that a combined occipital nerve and supraorbital nerve neurostimulation shows better efficacy than occipital nerve stimulation alone. Neuromodulation 19(5), 507-514 (2016) discloses that while patient functional status is improved in the perioperative period, it waned over the long-term follow-up. Cephalalgia 33(10), 816-830 (2013) discloses that sphenopalatine ganglion stimulation (SPG) yields positive results in several trials mainly for the treatment of cluster headache. However, although generally well tolerated, these invasive neuromodulation technics could be appropriate for intractable migraine and chronic cluster headaches, but may not be acceptable for less severe migraine patient categories. Cephalalgia 36(6), 534-546 (2016) discloses that non-invasive vagus nerve stimulation shows clinical benefits beyond those with standard of care for cluster headache. However, the Journal of Headache and Pain 16, 63 (2015) and Neurology 87(5), 529-538 (2016) report negative results for non-invasive vagus nerve stimulation from sham-controlled trials for chronic migraine.

BMC Neurology 11, 135 (2011) discloses a double-blind, sham-controlled, cross-over study with healthy subjects in which transcutaneous supraorbital neurostimulation was found to produce a sedative effect. Neurology 80(8), 697-704 (2013) discloses a subsequent multi-center, randomized, double-blind, sham-controlled trial which reveals the efficacy and safety of external trigeminal nerve stimulation (e-TNS) for the prevention of episodic migraine. The Journal of Headache and Pain 16, 69 (2015) discloses a larger open randomized trial in which the therapeutic efficacy in migraine prevention was corroborated. The Journal of Headache and Pain 14, 95 (2013) discloses a prospective study of 2313 patients in which safety and patient satisfaction have been further confirmed.

However, there remains a need in the art for a safe non-drug and non-invasive acute treatment for migraine attacks.

US 2009/0 210 028 discloses a device for the electrotherapeutic treatment of headaches such as tension headaches and migraines. An electrode support has a shape and is size selected so as to allow, independently from the subject, the excitation of the afferent paths of the supratrochlear and supraorbital nerves of the ophthalmic branch of the trigeminal nerve. An electrical circuit includes a programmable signal generator suitable for creating pulses of a duration of between 150 and 450 has with a maximum increase in intensity of 0 to 20 mA at a rate of less than or equal to 40 µA/s and with a step up in intensity not exceeding 50 µA.

US 2009/0 210 028 does not disclose the use of the device for the acute treatment of migraine attacks. In addition, US 2009/0 210 028 does not disclose particular treatment durations.

US 2010/0 274 327 discloses an electrotherapy system for stimulating sensory nerves within skin tissue. The system comprises an electrode carrier, a pulse generator, an array of skin-penetrating electrodes and surface skin electrodes, a pulse conditioning circuit, and a power source. The system administers biphasic pulsed current at the surface skin electrodes and monophasic pulsed current at each skin-penetrating electrode. The document in particular discloses the combined use of the skin-penetrating and surface skin electrodes. The embodiments disclosed in US 2010/0 274 327 provide an applicable electrode patch combining both the surface skin electrodes and skin-penetrating electrodes within this same patch. Non-invasive treatment is not possible with such an electrode patch. The system and in particular the surface skin electrodes are configured for masking pain due to stimulation via the skin-penetrating electrodes. The document does not disclose the treatment of migraine. The document also does not disclose the ophthalmic branch of the trigeminal nerve.

The present invention aims to resolve at least some of the problems mentioned above.

SUMMARY OF THE INVENTION

In a first aspect, the present invention provides a system for the acute non-invasive treatment of a migraine attack of a patient, as disclosed in claim 1.

In a second aspect, the present invention provides a method for the acute non-invasive treatment of a migraine attack of a patient, as disclosed in claim 15.

The present invention is advantageous as it provides a safe non-drug and non-invasive acute treatment method and system for migraine attacks, and thereby fills in a long felt need in the art. The invention is based on three clinical trials which are disclosed in the examples.

DETAILED DESCRIPTION OF THE INVENTION

Figure 1:
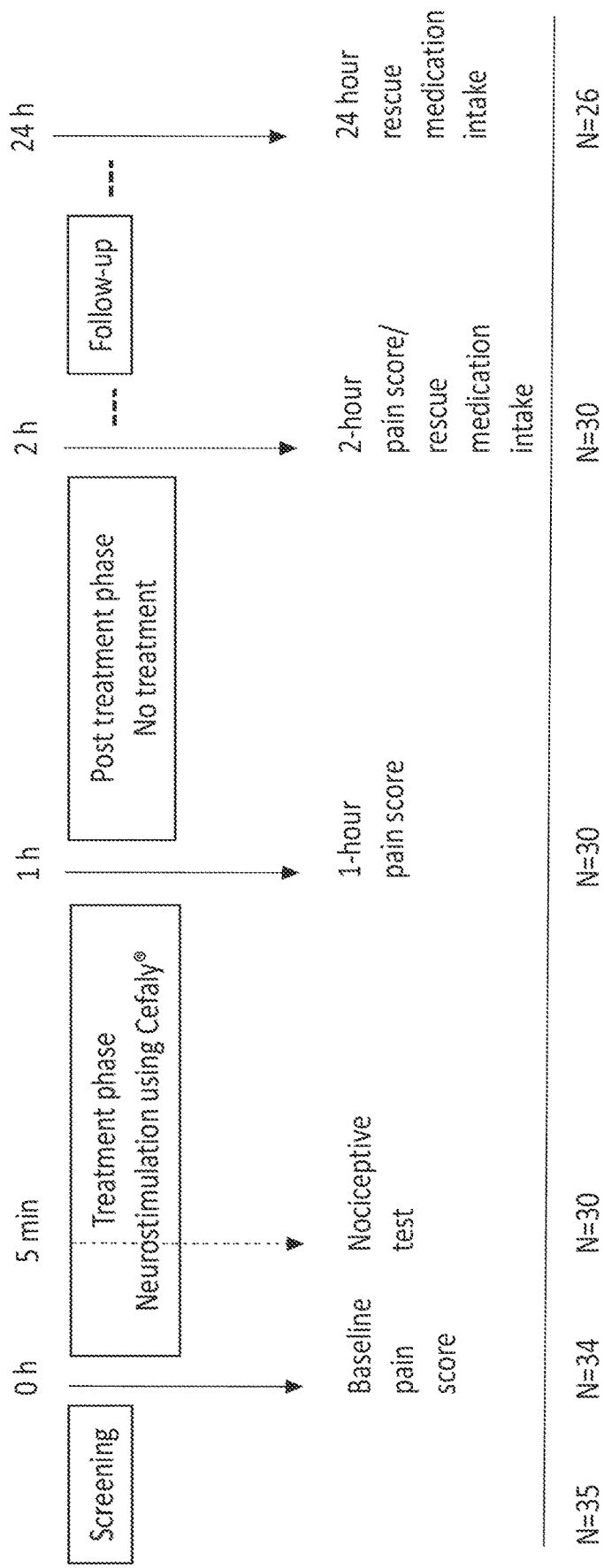
FIG. 1 shows a timeline of a prospective clinical trial.

The present invention concerns a system and a method for the acute non-invasive treatment of a migraine attack. The invention was summarized in the corresponding section. In what follows, the invention will be described in detail, preferred embodiments are elucidated, and the invention is illustrated by means of examples.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. The recitation of numerical ranges by endpoints includes all numbers and fractions subsumed within that range, as well as the recited endpoints.

In a first aspect, the invention provides a system for the acute non-invasive treatment of a migraine attack of a patient. The system comprises at least one skin electrode. The at least one skin electrode is configured for placement on the forehead of the patient. The system is configured for providing consecutive biphasic electrical pulses via said at least one skin electrode for a prolonged time span. Preferably, said time span is at least minutes, more preferably at least 25 minutes, even more preferably at least 35 minutes, yet even more preferably at least 45 minutes, and most preferably at least 55 minutes, such as a time span of 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240 minutes, or any value above or in between.

The applicant has found that a prolonged treatment, i.e. for at least 10 minutes and preferably at least about 60 minutes, is beneficial for the pain relief during migraine attacks, both with respect to immediate suppression of pain as well as prolonged pain relief after finishing the treatment. The clinical trials disclosed in the examples support this statement.

In a preferred embodiment, the biphasic electrical pulses are in essence rectangular biphasic pulses with a zero electrical mean. This is advantageous as these type of pulses are easy to generate and require no net charge transfer to the patient.

In a preferred embodiment, the system is configured for providing said consecutive biphasic electrical pulses at a frequency of at least 10 Hz and at most 300 Hz, such as 10 Hz, 20 Hz, 30 Hz, 40 Hz, 50 Hz, 60 Hz, 70 Hz, 80 Hz, 90 Hz, 100 Hz, 110 Hz, 120 Hz, 130 Hz, 140 Hz, 150 Hz, 160 Hz, 170 Hz, 180 Hz, 190 Hz, 200 Hz, 220 Hz, 240 Hz, 260 Hz, 280 Hz, 300 Hz, or any value in between.

The applicant had found that at a frequency of about 100 Hz, the pulses are best capable of generating an analgesic effect by exciting the trigeminal nerve, and more specifically the supratrochlear and supraorbital nerves of the ophthalmic branch of the trigeminal nerve, thereby relieving pain and treating the migraine attack.

In an embodiment, the system is configured for providing said consecutive biphasic electrical pulses at a frequency of at least 150 Hz and at most 500 Hz, such as 150 Hz, 160 Hz, 170 Hz, 180 Hz, 190 Hz, 200 Hz, 210 Hz, 220 Hz, 230 Hz, 240 Hz, 250 Hz, 260 Hz, 270 Hz, 280 Hz, 290 Hz, 300 Hz, 320 Hz, 340 Hz, 360 Hz, 380 Hz, 400 Hz, 420 Hz, 440 Hz, 460 Hz, 480 Hz, 500 Hz, or any value in between. Preferably, in this embodiment, the system is configured for providing said consecutive biphasic electrical pulses at a frequency of at least 200 Hz and at most 400 Hz, more preferably at least 240 Hz and at most 360 Hz, even more preferably at least 250 Hz and at most 350 Hz, yet even more preferably at least 260 Hz and at most 340 Hz, with greater preference at least 275 Hz and at most 325 Hz, with a yet even greater preference at least 290 Hz and at most 310 Hz, and most preferably about 300 Hz.

The applicant has performed preliminary tests indicating that tripling the frequency from about 100 Hz to about 300 Hz may improve the efficacy of the treatment further.

In a preferred embodiment, at least some, and preferably each, of said consecutive biphasic electrical pulses comprises a width of at least 30 μs and at most 1000 μs, preferably at least 100 μs and at most 500 μs, such as 100 μs, 125 μs, 150 μs, 175 μs, 200 μs, 225 μs, 250 μs, 275 μs, 300

μs, 325 μs, 350 μs, 375 μs, 400 μs, 425 μs, 450 μs, 475 μs, 500 μs, or any value in between.

The applicant has found that pulses comprising a width of about 250 μs induce a sufficient temporary charge build-up to be sufficiently effective to excite (trigger action potentials) the trigeminal nerve, and more specifically the supratrochlear and supraorbital nerves of the ophthalmic branch of the trigeminal nerve, thereby relieving pain and treating the migraine attack.

In a preferred embodiment, the system is configured for linearly increasing the amplitude of said consecutive biphasic electrical pulses during a first portion of said time span up to a preconfigured upper amplitude which is maintained during a second subsequent portion of said time span. Preferably, said preconfigured upper amplitude is at least 1 mA and at most 50 mA, more preferably at least 5 mA and at most 25 mA, such as 5 mA, 6 mA, 7 mA, 8 mA, 9 mA, 10 mA, 11 mA, 12 mA, 13 mA, 14 mA, 15 mA, 16 mA, 17 mA, 18 mA, 19 mA, 20 mA, 21 mA, 22 mA, 23 mA, 24, mA, 25 mA, or any value in between. Preferably, said first portion of said time span is at least 1 minute and at most 30 minutes, more preferably at least 5 minutes and at most 20 minutes, such as 5, 6, 7, 8, 9, 10, 11, 12, 13, 14, 15, 16, 17, 18, 19, 20 minutes, or any value in between. Preferably, said linear amplitude increase during said first portion of said time span comprises a slope of at least 1.6 μA/s and at most 833 μA/s, preferably at least 8 μA/s and at most 83 μA/s, such as 8, 9, 10, 11, 12, 13, 14, 15, 16, 17, 18, 19, 20, 21, 22, 23, 24, 25, 26, 27, 28, 29, 30 μA/s, or any value in between. Most preferably, the amplitude is ramped up from 0 mA to about 16 mA in about 14 minutes, the slope of the linear amplitude increase thereby comprising a value of about 19 μA/s.

The applicant has found that an amplitude of the pulses of about 16 mA allows the maximum space recruitment, i.e. excitation (stimulation) of all nerve fibers of the supratrochlear and supraorbital nerves, and thus poses an optimal effectiveness of the treatment. The gentle linear ramp-up up to the preconfigured upper amplitude is advantageous as it helps the patient to ease into the strong preconfigured upper stimulation amplitude of 16 mA.

In a preferred embodiment, the system comprises a patient-pushable button. The system is hereby configured upon shortly pushing of said button during said time span for maintaining the provided biphasic pulse amplitude at or prior to the time of said pushing of said button throughout the reminder of said time span. This is advantageous as it allows a patient, during the gentle ramp-up up to the preconfigured upper amplitude, to push the button to maintain the current or a previous amplitude during the reminder of the treatment time. A patient can hence limit the intensity should it become too high.

In a preferred embodiment, the system is further configured for acceleration of the ramp-up upon continuously pushing of said button for several seconds. This is advantageous as a patient who is used to treatment of migraine attacks by means of the system can get a speedier ramp-up and thus faster headache relief. By pressing said button continuously for several seconds, the optimal and most effective amplitude of 16 mA can be reached within 30 seconds. The system is hereby configured to increase the amplitude rapidly while the button is being continuously pushed. When the switch is subsequently released, the amplitude stabilizes and remains constant. By pressing the button again, the intensity increases again as long as the button is pushed.

Figure 2A:
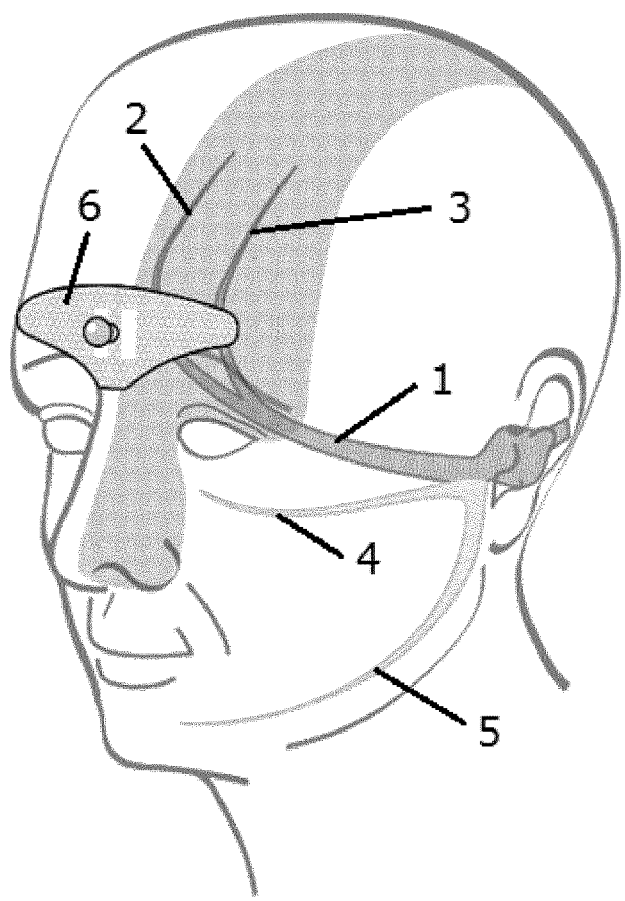
FIG. 2A shows a bipolar self-adhesive electrode attached to a forehead of a patient, on which a power providing device can be placed, as shown in FIGS. 2B and 2C.
Figure 2B:
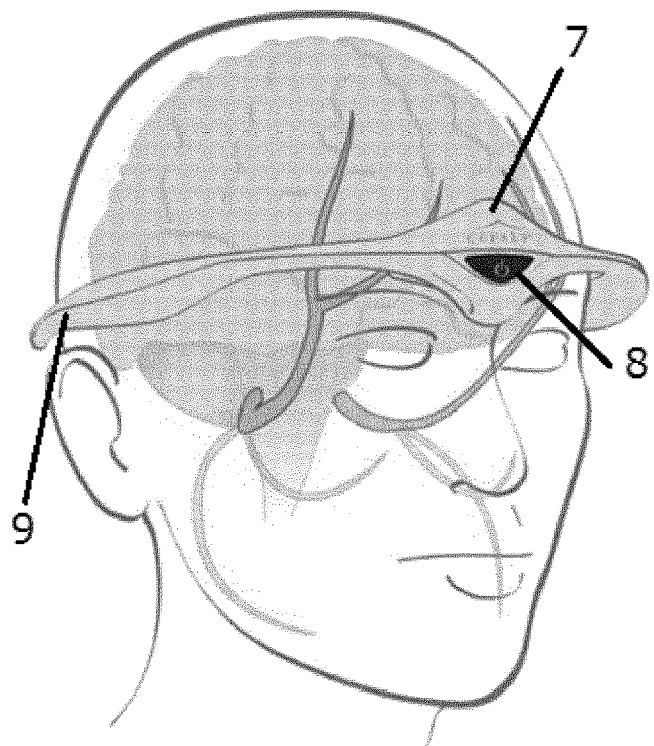
FIG. 2D shows an alternative bipolar self-adhesive electrode attached to a forehead of a patient.
Figure 4:
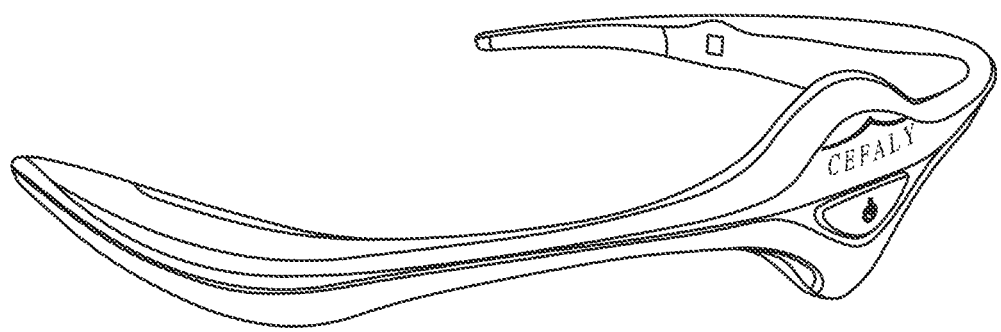
FIG. 4 shows a power-providing device.
Figure 5:
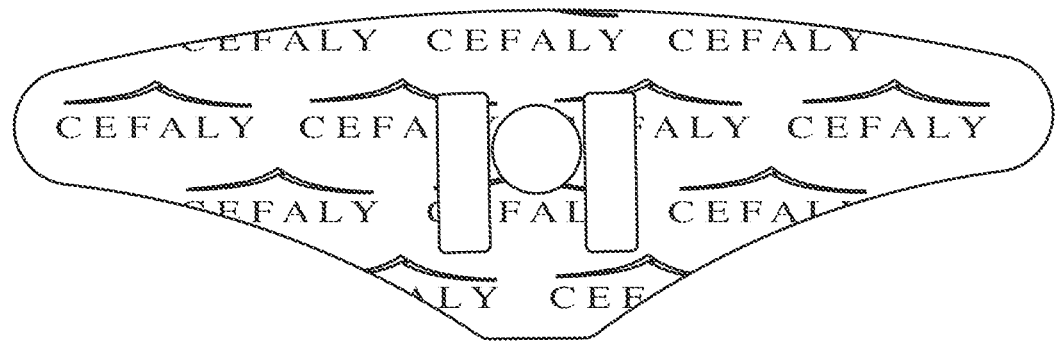
FIG. 5 shows a bipolar self-adhesive electrode.

In an embodiment, the at least one skin electrode may comprise two or more skin electrodes configured for attachment on the patient's forehead for establishing two or more contacts for providing said consecutive biphasic electrical pulses. In a most preferred embodiment, the at least one skin electrode comprises a bipolar self-adhesive electrode, comprising a self-adhesive side for skin contact and an outer side comprising two contact areas for establishing electrical contact with an energy-providing device. FIG. 5 shows an embodiment of such a bipolar self-adhesive skin electrode. It furthermore comprises a central protrusion over which an energy-providing device can be positioned. FIG. 2A shows the positioning of a bipolar self-adhesive skin electrode (6) on the forehead of a patient. The bipolar self-adhesive skin electrode (6) and its positioning are thereby adapted for stimulation of the trigeminal nerve, which has three branches: the ophthalmic branch (1), the maxillary branch (4), and the mandibular branch (5). This nerve divides into two branches on the forehead: the internal frontal (or supratrochlear) nerve (2) and the external frontal (or supraorbital) nerve (3). The bipolar self-adhesive skin electrode comprises in particular a shape and configuration adapted for stimulation of the supratrochlear and supraorbital nerves of the ophthalmic branch of the trigeminal nerve. FIG. 4 shows an embodiment of a head-clampable device comprising two metallic contacts (not shown) which can be positioned in electrical contact with the two contact areas of said bipolar self-adhesive skin electrode. The head-clampable device comprises a recess for placement over the protrusion of the bipolar self-adhesive skin electrode. The protrusion can thereby comprise a base connected on one end to the outer surface of the skin electrode and ending on the opposite end in a broader head. The recess of the head-clampable device is preferably configured for stable placement over said broader head. FIG. 2B illustrates the placement of the head-clampable device (7) over the bipolar skin electrode. The device comprises a button (8) for starting a treatment and/or for limiting of said amplitude during said linear increase in said first portion of said time span. The head-clampable device of FIG. 2B comprises two legs (9) to provide the clamping functionality. Alternatively, the clamping functionality may also be realized by an elastic band. Each of said legs also comprises a compartment for positioning of one AAA-type battery for powering the device. The system comprising the device and the at least one skin electrode is thereby portable, i.e. a patient can walk around and has his/her hands free.

Figure 2C:
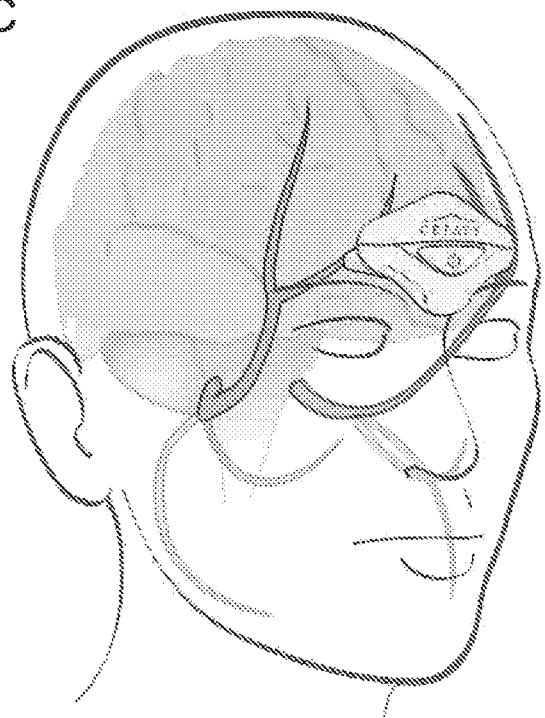

An alternative embodiment of a power-providing device is shown in FIG. 2C. The bipolar self-adhesive skin electrode comprises a protrusion comprising a base connected on one end to the outer surface of the skin electrode and ending on the opposite end in a broader head. The power-providing device comprises a recess for stable placement of the device over the head of the protrusion. As can be seen in FIG. 2C, the device is thereby legless. The device also comprises at least one compartment for the positioning of at least one battery. Alternatively, the device comprises an internal rechargeable battery. The device also comprises a button for starting a treatment and/or for limiting of said amplitude during said linear increase in said first portion of said time span. The system comprising the device and the at least one skin electrode is thereby also portable, i.e. a patient can walk around and has his/her hands free.

Figure 2D:
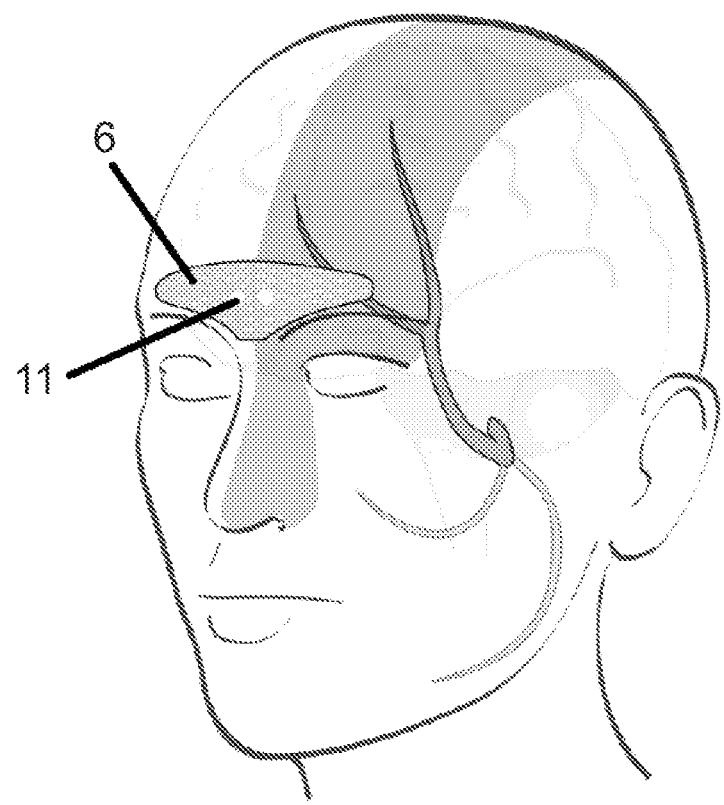
Figure 6:
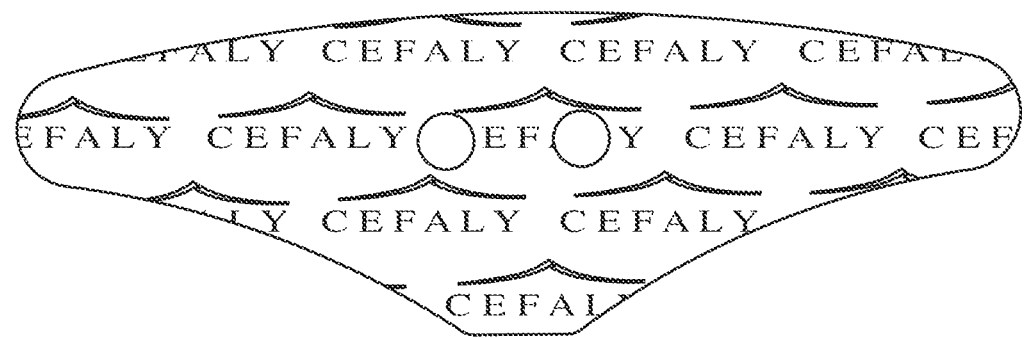
FIG. 6 shows an alternative bipolar self-adhesive electrode.
Figure 7:
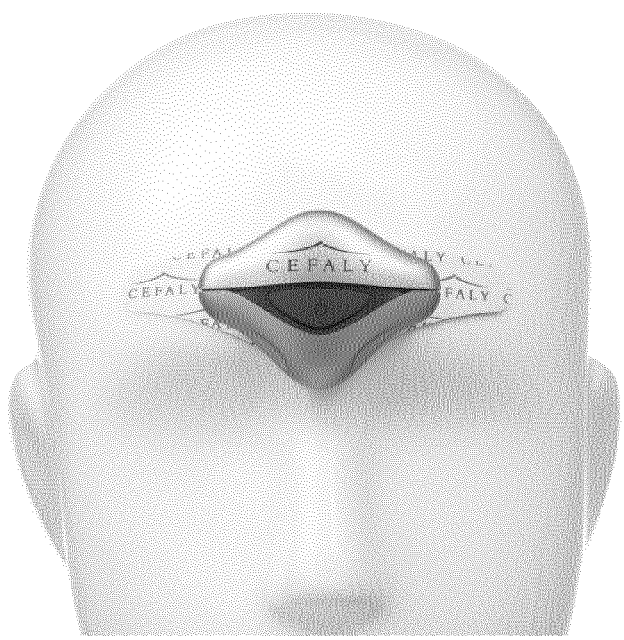
FIG. 7 shows a power-providing device attached to the bipolar self-adhesive electrode shown in FIG. 6.

In another embodiment, the at least one skin electrode comprises a bipolar self-adhesive electrode, comprising a self-adhesive side for skin contact and an outer side comprising two metallic contacts for establishing electrical contact as well as attachment with an energy-providing device. The self-adhesive side may comprise two self-adhesive electrode regions. FIG. 6 shows an embodiment of such a bipolar self-adhesive skin electrode. FIG. 2D shows the positioning on a forehead of a bipolar self-adhesive skin electrode (6) comprising two metallic contact areas (11). As before, the bipolar self-adhesive skin electrode and its positioning are thereby adapted for stimulation of the trigeminal nerve, and preferably for stimulation of the supratrochlear and supraorbital nerves of the ophthalmic branch of the trigeminal nerve. FIG. 7 shows an embodiment of a power-providing device comprising two metallic contacts (not shown) positioned in electrical contact with the two metallic contact areas of said bipolar self-adhesive skin electrode. Preferably, the metallic contacts of the bipolar self-adhesive electrode or the power-providing device are magnetic for attachment of the power-providing device to the bipolar self-adhesive skin electrode. The power-providing device comprises a button for starting a treatment and/or for limiting of said amplitude during said linear increase in said first portion of said time span. Preferably, the system is portable, i.e. a patient can walk around and has his/her hands free. Preferably, the power-providing device is legless. Preferably, the power-providing device comprises a rechargeable battery.

Preferably, the power-providing device is lightweight, more preferably comprising a weight smaller than 100 g, such as a weight of 12 g. Preferably, the power-providing device is compact, more preferably comprising dimensions smaller than 80 mm×80 mm×30 mm, such as dimensions of 55 mm×40 mm×15 mm. Preferably, the bipolar self-adhesive electrode comprises a length of in between 50 mm and 150 mm, such as a length of 94 mm. Preferably, the bipolar self-adhesive electrode comprises a height of in between 10 mm and 50 mm, such as a height of 30 mm. Preferably, the bipolar self-adhesive electrode comprises hypoallergenic gel.

In a preferred embodiment, the power-providing device comprises a processing unit, a tangible non-transitory computer-readable storage medium, and computer-readable instructions for storing information about a treatment session on the storage medium. The power-providing device may comprise a cable port or module for wireless communication for data read-out of said stored information. The cable port may be a USB port. The module for wireless communication may be a Bluetooth module.

In a preferred embodiment, the system comprises a tangible non-transitory storage medium, such as, for example, a programmable electrical circuit, for setting and storing at least one and preferably all of: the pulse frequency, the pulse width, the pulse amplitude, the pulse ramp-up time or ramp-up slope for linear increase of the amplitude, and the treatment time (i.e. the time span).

The system of the first aspect of the invention may also be part of a kit, whereby the kit also comprises a medication. Preferably, the medication comprises one or more of an analgesic, a non-steroidal anti-inflammatory drug, a triptan, a ditan, and a CGRP antagonist. Depending on the needs of a patient, the patient may use a combined treatment comprising the medication and the e-TNS. The combined treatment may comprise the starting of the e-TNS treatment and the intake of the medication at about the same time. The combined treatment may comprise the intake of the medication during or after the e-TNS treatment, when, for example, the e-TNS treatment alone does not seem sufficiently effective for the patient.

In a second aspect, the invention provides a method for the acute non-invasive treatment of a migraine attack of a patient. The patient comprises a forehead, a supratrochlear nerve, and a supraorbital nerve. The method comprises the steps of (a) placing at least one skin electrode on the forehead of the patient and (b) providing consecutive biphasic electrical pulses via said at least one skin electrode to said supratrochlear and said supraorbital nerves for a prolonged time span.

One of ordinary skill in the art will appreciate that all preferred embodiments in relation to the system also pertain to the method. Preferably, said at least one skin electrode comprises a bipolar self-adhesive electrode, as noted above. Preferably, said time span is at least 25 minutes. Preferably, said biphasic electrical pulses are in essence rectangular biphasic symmetrical pulses with a zero electrical mean. Preferably, said consecutive biphasic electrical pulses are provided at a frequency of about 100 Hz. In an alternative preferential embodiment, said consecutive biphasic electrical pulses are provided at a frequency of about 300 Hz. Preferably, each of said consecutive biphasic electrical pulses comprising a width of about 250 μs. Preferably, said consecutive biphasic electrical pulses comprise an amplitude which increases linearly over a first portion of said time span up to an upper amplitude which is maintained during a second subsequent portion of said time span, preferably said upper amplitude one of a predefined upper amplitude of about 16 mA or a patient-determined upper amplitude (button push) of at most 16 mA, preferably the slope of said linear increase about 19 μA/s.

The invention is further described by the following non-limiting examples which further illustrate the invention, and are not intended to, nor should they be interpreted to, limit the scope of the invention.

EXAMPLES

Example 1: Prospective Clinical Trial

A monocentric, prospective, open-labelled clinical trial was conducted at the Columbia University Headache Center (NY, USA). The study was approved by the ethics committee at Columbia University Medical Center (IRB-AAA09752) and registered on ClinicalTrials.gov (identifier: NCT02411513). Written informed consent was obtained from all patients included in the study.

Patients with migraine with or without aura were recruited at a standard care visit or from home if they were experiencing a migraine attack lasting for at least three hours, with pain intensity stabilized for at least one hour and no intake of acute migraine medications for the prior three hours. Inclusion criteria were the following: adult patients aged 18 to 65 years with a history of episodic or chronic migraine with or without aura, meeting the diagnostic criteria listed in the International Classification of Headache Disorders $3^{rd}$ edition (beta version) (ICHD-III beta, 2013) section 1, migraine (https://www.ichd-3.org/1-migraine/) with the exception of "complicated migraine" (i.e., hemiplegic migraine, migraine with brainstem aura, ophthalmoplegic migraine/recurrent painful ophthalmoplegic neuropathy, migrainous infarction), experiencing headache localized to the frontal, retro- or peri-orbital region(s), on one or either side. Exclusion criteria were the following: (1) pregnancy; (2) treatment with onabotulinum toxin (e.g., Botox, Dysport, Xeomin) to the head in the prior four months; (3) supraorbital nerve blocks in the prior four months; (4) diagnosis of other primary or secondary headache disorders, except of medication overuse headache; (5) only temporal or occipital headache location; (6) use of opioids in the preceding three months; (7) use of abortive migraine medication within three hours prior to enrollment; (8) intolerance to supraorbital neurostimulation (allodynia); (9) implanted metal or electrical devices in the head; and (10) cardiac pacemaker or implanted or wearable defibrillator.

Patients were asked to rate their pain severity (baseline score) using an eleven-point visual analogue scale (VAS) (from 0=no pain to 10=maximum pain). The e-TNS device was then applied and neurostimulation treatment was initiated with intensity increasing over the first 14 minutes. Patients who were able to tolerate the paresthesia sensation for the first five minutes (thus reaching a minimum intensity of 7 mA or a minimum electrical dose of 1.75 pC per impulse) without having to level off the intensity were included and subsequently continued neurostimulation for the 55 remaining minutes. Those patients who were unable to tolerate the initial test phase were not enrolled, on the basis of the allodynia exclusion criterion (low nociceptive forehead skin threshold). At the completion of the one-hour treatment phase, patients were asked to rate their pain intensity (one-hour score) and again one hour post-treatment (two-hour score). Use of rescue medications was recorded at the two-hour mark; patients were also contacted the following day regarding use of rescue medications within 24 hours following the e-TNS treatment. Patients who took rescue medication before the end of the post-treatment phase were deemed a drop-out. The study design is illustrated in FIG. 1.

External trigeminal nerve stimulation (e-TNS) was applied via the Cefaly® neurostimulator device (CEFALY Technology, Seraing, Belgium) for a 60-minute treatment session. The device is a constant current generator for a maximum skin impedance of 2.2 kΩ that delivers rectangular biphasic symmetrical pulses with a zero electrical mean. In the current study, the device was programmed with a pulse frequency of 100 Hz and a pulse width of 250 has; the total maximum dose of current delivered by a one-hour treatment session is 1.284 Coulomb. The electrical impulses are transmitted transcutaneously via a supraorbital bipolar electrode (30 mm×94 mm) designed to cover and excite (trigger action potentials) on both sides of the supratrochlearis and supraorbitalis nerves (see FIGS. 2 and 5). The intensity increases linearly to reach a maximum of 16 mA after 14 minutes and then stays constant for 46 minutes. If the patient feels that the stimulation is too strong, a single press on the device's button will stabilize the intensity for the remainder of the session (in this event, the patient receives a lower total current dosage).

Patients scored their pain intensity on a visual analogue scale (VAS) with eleven levels (from 0=no pain to 10=maximum pain). Pain level was assessed before the treatment was applied (baseline score), after the one-hour treatment (1 h score) and at two hours after the beginning of the treatment phase (2 h score). Rescue medication intake was also recorded at 2 and 24 hours. Primary outcome was the mean change in pain intensity after the one-hour treatment, compared to baseline. Secondary outcomes were mean change in pain intensity at two hours after the start of treatment compared to baseline, as well as the percentage of patients not requiring rescue medication at two and 24 hours following the treatment.

Analyses were conducted on a modified intention-to-treat (mITT) basis, i.e. the eligible population consisted of patients having administered the treatment and for which there were a baseline severity measurement. For each patient, the outcome was calculated on all data available during each period, without any imputation of missing data. Comparison between baseline and treatment results was performed using the Wilcoxon Signed Rank test for paired samples.

TABLE 1 patient demographic characteristics

| | |
|---|---|
| Number of patients included | 30 |
| Age (years) | 39.42 ± 12.49 |
| Number of female | 24 (80.00 %) |

Data are expressed as number, mean ± SD or number (%).

The trial was conducted from April 2015 through October 2015. In total, 35 patients were screened. One patient was excluded due to use of opioid medication within the prior three months and four patients failed the nociceptive test (two patients were not able to tolerate early stimulation and two patients were excluded due to unintentional disconnection of the device from the electrode by the patient during the test phase). The remaining 30 patients received the full one-hour stimulation, with zero drop-out during the study (see FIG. 1). Patient demographic characteristics are shown in Table 1. No adverse events occurred, nor were any subjective complaints reported during or within 24 hours after the treatment.

Table 2 presents the study outcomes. There was a statistically significant decrease in pain intensity, both after the one-hour treatment and at two hours after treatment initiation. No patients used rescue medication at the end of the two-hour period. Patients were also contacted 24 hours after the treatment to report whether they used rescue medication during that time frame. Of the 26 patients who were successfully contacted, 17 patients (65.4%) did not use rescue medication within the 24 hours following the treatment.

TABLE 2

Study outcomes

| Primary outcome | |
|---|---|
| Change in pain intensity after 1 hour of treatment, compared to baseline | −3.22 ± 2.40 (p < 0.001*) |
| Secondary outcomes | |
| Change in pain intensity 2 hours after treatment initiation, compared to baseline | −2.98 ± 2.31 (p < 0.001*) |
| Percentage of patients not having required rescue medication at 2 hours | 100.00% |
| Percentage of patients not having required rescue medication within 24 hours** | 65.38% |
| Supplementary results | |
| Patients reporting ≥ 30% pain relief at 1 hour | 25 (83.33%) |
| Patients reporting ≥ 30% pain relief at 2 hours | 21 (70.00%) |
| Patients reporting ≥ 50% pain relief at 1 hour | 23 (76.67%) |
| Patients reporting ≥ 50% pain relief at 2 hours | 17 (56.67%) |
| Patients reporting pain freedom at 1 hour | 6 (20.00%) |
| Patients reporting pain freedom at 2 hours | 4 (13.33%) |

Figure 3:
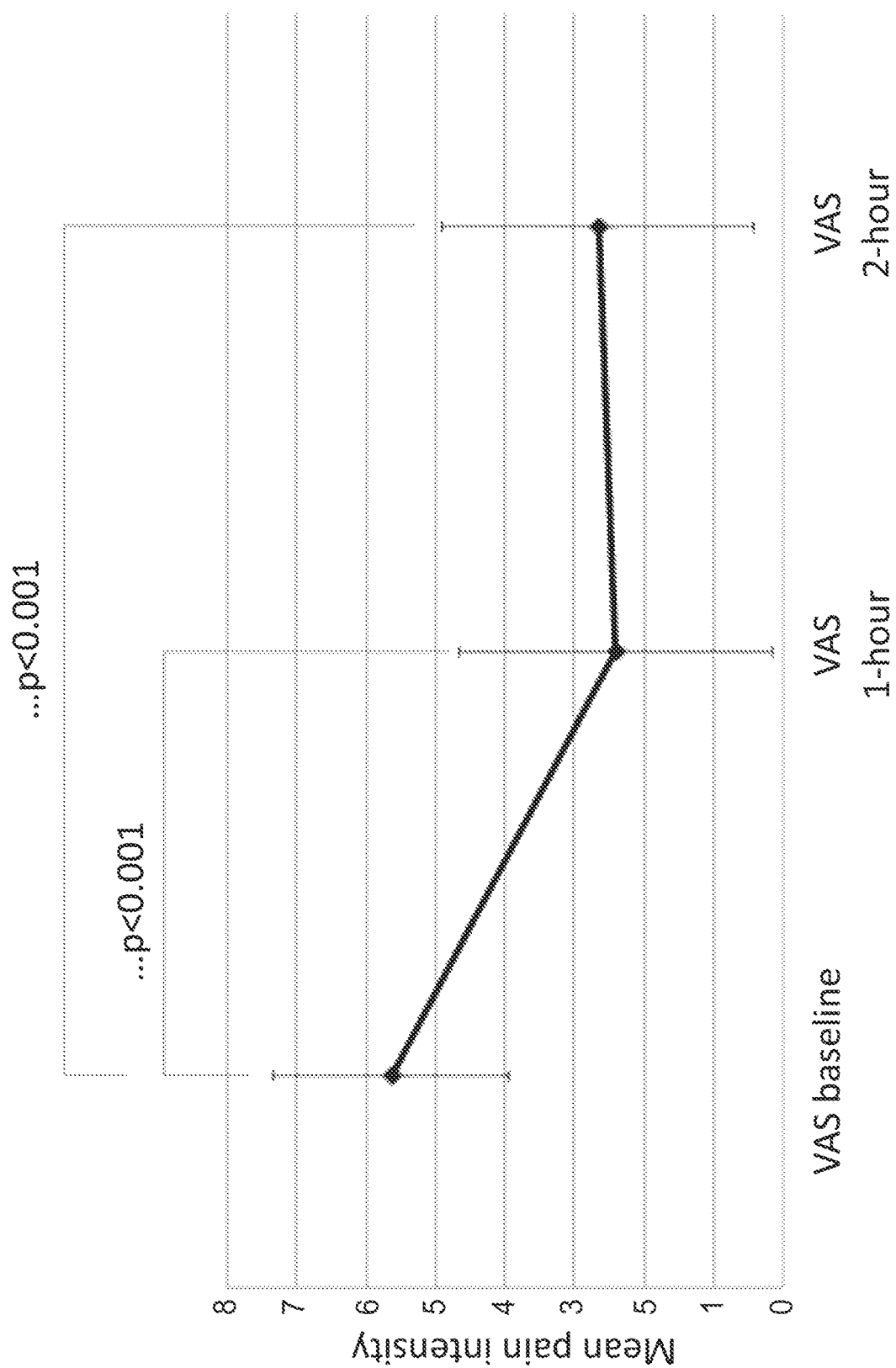
FIG. 3 shows the time evolution of a mean pain intensity in a prospective clinical trial.

Data are expressed as mean ± SD, % or number (%).
*P-values were calculated using the Wilcoxon Signed Rank test for paired samples.
**Missing data for 4 patients FIG. 3 presents the change in mean pain intensity. On average, pain intensity was reduced from 5.63 to 2.42 after one hour of treatment and to 2.66 at two hours. This reduction was statistically significant in both cases (p<0.001).

As shown in Table 2, 76.7% of patients reported 50% pain relief at one hour and 56.7% at two hours. Six patients (20.0%) reported pain freedom at one hour, and four patients (13.3%) at two hours.

Regarding the neurostimulation intensity, 17 patients (56.7%) tolerated the maximum intensity of 16 mA (i.e. received the full dose of current of 1.284 Coulomb) and 13 patients (43.3%) required the stimulation intensity to be limited at an average of 9.51 mA. Sub-analysis comparing the group of 13 patients who limited the current output and the group of 17 patients who received the total electrical dose revealed a difference only in use of rescue medication intake within 24 hours: 50% of patients receiving partial current output used rescue medication, compared to 25% of patients who received the full current dose. However, data were only available for 10 and 16 patients in each group, respectively, and the difference was not statistically significant (p=0.234). Baseline pain scores were similar between the two groups (p=0.240): mean score of 6.0 for the 13 patients who limited current output during the stimulation vs. mean score of 5.4 for the 17 patients who received the total electrical dose.

Concerning safety, no adverse events (AEs) or complaints were reported during the trial, which confirms the high safety level of the treatment. J. Headache Pain 14, 95 (2013) also demonstrated the safety in a retrospective study on the prevention of episodic migraine in 2313 patients, of whom only 4.3% reported adverse effects (including 2.03% with intolerance to paresthesia). In our study, 2 out of 34 patients (5.9%) were not enrolled due to failure of the tolerance test. This higher percentage of intolerance to paresthesia could be explained by increased allodynia during migraine attacks. Interestingly, there was no increase in skin irritation with the longer 60-minute session, compared to the 20-minute session used in prior studies.

With regards to efficacy, mean pain intensity was significantly reduced by 57.0% after the one-hour treatment and by 52.8% at two hours. The similar rate at the two time points indicates that pain reduction is well-maintained for at least an hour after the end of the neurostimulation. The percentage of patients not using rescue medication was 100% after two hours and 65.4% after 24 hours. The proportion of patients not taking rescue medication within 24 hours in a placebo group for the acute treatment of migraine with medication is usually reported to be around 32%, nevertheless the populations are not the same and the treatment protocols are different which make any comparison difficult. Therefore these efficacy data are promising, although it should be taken into account that the study was open-labelled and treatment in a clinic setting may accentuate the placebo effect. On the other hand, treatment in a clinic ensures appropriate application/use of the device and proper collection of data. Of further consideration is that patients were recruited at a minimum of three hours into a migraine attack to ensure a stable baseline pain intensity; however, it is known that acute pharmacologic treatments are more effective when used earlier in a migraine attack. The effectiveness of the e-TNS device even when used late in a migraine attack is thus encouraging.

Comparison with published data for other acute migraine treatments is limited because of differences in trial design. Nevertheless, Cephalalgia 19(4), 232-240 (1999) reported a reduction in mean pain VAS scores at one hour of 26.8% for diclofenac and 17.1% for sumatriptan, compared to 57.1% for e-TNS in our study. At two hours, mean pain score reductions were 50.5% for diclofenac, 40.0% for sumatriptan and 52.7% with e-TNS.

Regarding rescue medication intake, Headache 55 Suppl 4, 221-235 (2015), a recent review on triptans for the acute treatment of migraine, reported that use of rescue medication after a standard dose triptan ranged from 20 to 34% and averaged 37% for NSAIDs, versus 34.6% for e-TNS between 2 and 24 hours. Notwithstanding the limitation of these comparisons due to differences in study design, the data suggest a similarity in efficacy with respect to rescue medication use. Again, it should be noted that the e-TNS treatment was applied later in a migraine attack (at least 3 hours) than the above acute migraine medications, which have shown better efficacy when administered early into an attack.

Example 2: External Trigeminal Nerve Stimulation Device

The device is a small, portable product comprising legs, which is meant to be worn on the forehead by attachment to a bipolar self-adhesive electrode on the forehead (Figures 2, 4 and 5). The electrode comprises a length of about 94 mm and a height of about 30 mm. Two 1.5V AAA batteries provide power to the device.

The device is an external cranial neurostimulator designed for supraorbital neurostimulation (also known as external trigeminal nerve stimulation or e-TNS). The electrode is designed in order to cover both sides of the supratrochlearis and supraorbitalis nerves, which are branches of the trigeminal nerve. Trigeminal nerve stimulation induces a sedative effect on the central nervous system. The electrical impulses generated by the device trigger signals (action potentials) on the supratrochlear and supraorbital nerves of trigeminal nerve. Repetitive excitation of the trigeminal nerve is a neuromodulation of the trigeminal system. Neuromodulation of the trigeminal system induces a sedative effect on the central nervous system and a trigeminal nociceptive threshold modification.

The device will preferably run sessions of about 60 minutes, during which it generates very precise electrical impulses that permit stimulation of the nerve fibers. The electrical impulses are transmitted transcutaneously via the bipolar self-adhesive electrode placed on the forehead. The device thereto comprises two metallic contacts which can be positioned in connection with two conductive areas on the bipolar self-adhesive electrode. The device delivers energy in the form of rectangular biphasic pulses. The intensity is increasing linearly to reach a maximum of about 16 mA after about 14 minutes (and then stays constant for about 46 minutes). The pulse frequency is about 100 Hz. The pulse width is about 250 has. The device is provided with a button, which upon pressing the button, enables a user to stabilize the intensity if the user feels that the intensity becomes too high.

The legs of the device can be configured for clamping around the sides of a patient's head. The two legs may thereto each comprise a plastic anti-slip layer. The legs of the device may in addition, or alternatively, be configured for support on the ears of a patient's head.

In an embodiment, the device and the electrode may be marketed under the registered trademark Cefaly® and/or Cefaly® Acute.

Example 3: Double-Blind Randomized Sham-Controlled Trial

The main objective of this study was to assess the efficacy and safety of the device disclosed in example 2 as an acute treatment of migraine attacks with or without aura (International Classification of Headache Disorders [ICHD]-III beta (2013) section 1) in patients from 18 to 65 years old, in a multi-center, double-blind, randomized, sham-controlled trial.

The multi-center, prospective, double-blind, randomized, sham-controlled clinical trial was conducted in 3 investigation sites. Eligible patients were randomized 1:1 to verum or sham stimulation and treated with the device during a 1-hour e-TNS treatment session at the clinic. Pain intensity was scored by the patient using a visual analogue scale (VAS) before the treatment, after the 1-hour treatment session, at 2-hour after the beginning of the treatment initiation and finally at 24-hour after the beginning of the treatment initiation. Anti-migraine rescue medication intake was recorded during the 24 hours following the beginning of the e-TNS treatment. During the different phases, the investigator monitored the possible occurrence of adverse events (AE). The primary outcome measure was the mean change of pain score at 1-hour time point compared to baseline. Secondary outcome measures were the mean change of pain score at 2-hour and 24-hour time points compared to baseline, the proportion of patients not having required anti-migraine rescue medication within the 24 hours after the beginning of the e-TNS treatment.

One hundred and six (106) patients having a migraine attack with or without aura were randomized and included in the intention-to-treat (ITT) analysis. Among them, ninety-nine (99) were eligible for the modified intention-to-treat (mITT) analysis, i.e. the randomized patients having had the 1-hour stimulation treatment and having given their headache pain intensity measurement at baseline and at 1-hour time points.

In terms of safety, one adverse event (nausea) occurred but this event was minor and totally reversible (nausea resolved by itself after 20 minutes). There was no serious adverse events (SAE), nor were any subjective complaints or side effects reported in either group within the 24 hours after the beginning of the treatment.

In terms of efficacy, in the ITT analysis, the primary outcome, mean migraine pain intensity after the 1-hour e-TNS session compared to baseline, was very significantly more reduced in the verum group than in the sham group (−3.46±2.32 versus −1.78±1.89, $p<0.001$; or −59% versus −30%, $p<0.001$). This pain relief percentage was as well significantly reduced in the verum group compared to the sham group at 2 hours and 24 hours. In the mITT analysis, mean migraine pain intensity was as well very significantly more reduced in the verum group than in the sham group at the 1-hour (−3.83±2.13 versus −1.85±1.89, $p<0.001$; or −65% versus −32%, $p<0.001$) and at the 2-hour and 24-hour time points. In addition, the percentage of pain-free patients at the 24-hour time point was significantly higher in the verum group compared with the sham group (32% versus 13%, $p<0.05$), and 30% sustained pain relief for 24 hours was significantly higher in the verum group compared to the sham group (43% versus 21%, $p<0.05$). Anti-migraine rescue medication intake within the 24 hours after the beginning of the treatment was not significantly lower in the verum group.

Example 4: Acute Non-Invasive Treatment at Home

The present example focuses on the acute non-invasive treatment of a migraine attack at an early stage of its development, at home, and provides an overview of a mono-center, prospective, open-label, phase-1 clinical trial.

4.1 Treatment System

The treatment system comprises a bipolar self-adhesive skin electrode and a power-providing device as shown in FIGS. 2C, 2D, 6 and 7 and as discussed above in conjunction with FIGS. 2C, 2D, 6 and 7. The power-providing device comprises a rechargeable battery. The power-providing device is configured to deliver rectangular biphasic pulses at a frequency of about 100 Hz and comprising a width of about 250 has. The power-providing device is configured to increase the pulse intensity linearly from 0 mA to a maximum of about 16 mA, during the initial about 14 minutes of a treatment session, and to maintain the pulse intensity of about 16 mA subsequently for about 106 minutes. The power-providing device comprises a tangible non-transitory computer-readable storage system for storing information about a treatment session.

The electrical pulses generated via the power-providing device run through the metallic contacts of the device and the skin electrode in order to carry out excitation on the supratrochlear and supraorbital nerves of the trigeminal nerve. Repetitive excitation of the trigeminal nerve is a neuromodulation of the trigeminal system, inducing a sedative effect on the central nervous system and a trigeminal nociceptive threshold modification, which causes headache pain relief during migraine attacks.

4.2 Study Measures

Headache pain severity: In order to evaluate the modification of pain severity from baseline to 2-hour and 24-hour time points, patients were asked to note their headache pain intensity on the following scale: grade 0=no pain; grade 1=mild pain; grade 2=moderate pain; and grade 3=severe pain.

Migraine associated symptoms: The patient also noted the presence of migraine associated symptoms (photophobia, phonophobia, nausea, vomiting) and specified which associated symptom is the most bothersome symptom (MBS) at baseline.

Rescue medication intake: The patient also recorded the intake of ANY acute rescue medication during the 24 hours following the beginning of the e-TNS session.

4.3 Population Criteria

The following inclusion criteria have been applied:
1. Age from 18 to 65 years on the day of signing the informed consent form
2. ≥1-year history of migraine with or without aura according to the diagnostic criteria listed in ICHDIII beta (2013) section 1, migraine (8), with the exception of aura without headache, hemiplegic migraine and brainstem aura migraine
3. Migraine onset before the age of 50 years
4. Having between 2 and 8 moderate or severe migraine attacks (grade 2 or 3) per month in each of the two months prior to screening
5. Patient understands the study procedures, alternative treatments available, and voluntarily agrees to participate in the study by giving written informed consent
6. Patient is able to read and understand the written information (instruction sheet, paper diary and AE collecting form)

The following exclusion criteria have been applied:
1. Patient has difficulty distinguishing his/her migraine attacks from tension-type headaches
2. Patient has more than 15 headache days per month
3. Patient having received supraorbital nerve blocks in the prior 4 months 4. Patient having received Botox treatment in the prior 4 months
5. Modification of a migraine prophylaxis treatment in the previous 3 months
6. Diagnosis of other primary headache disorders, except rare tension-type headaches (<4 per month)
7. Diagnosis of secondary headache disorders included Medication Overuse Headache
8. Patients abusing opioids or user of recreational or illicit drugs or has had a recent history (within the last year) of drug or alcohol abuse or dependence
9. Implanted metallic or electronic device in the head
10. Cardiac pacemaker or implanted or wearable defibrillator
11. Patient having had a previous experience with a Cefaly® device
12. Migraine Aura without headache
13. Patient is currently participating or has participated in a study with an investigational compound or device within 30 days of screening visit
14. Patients not having the ability to use appropriately the treatment system and/or to perform themselves or bear a first 20-minute stimulation session during a training session at the study site

4.4 Study Protocol

4.4.1 Recruitment Phase

Figure 8:
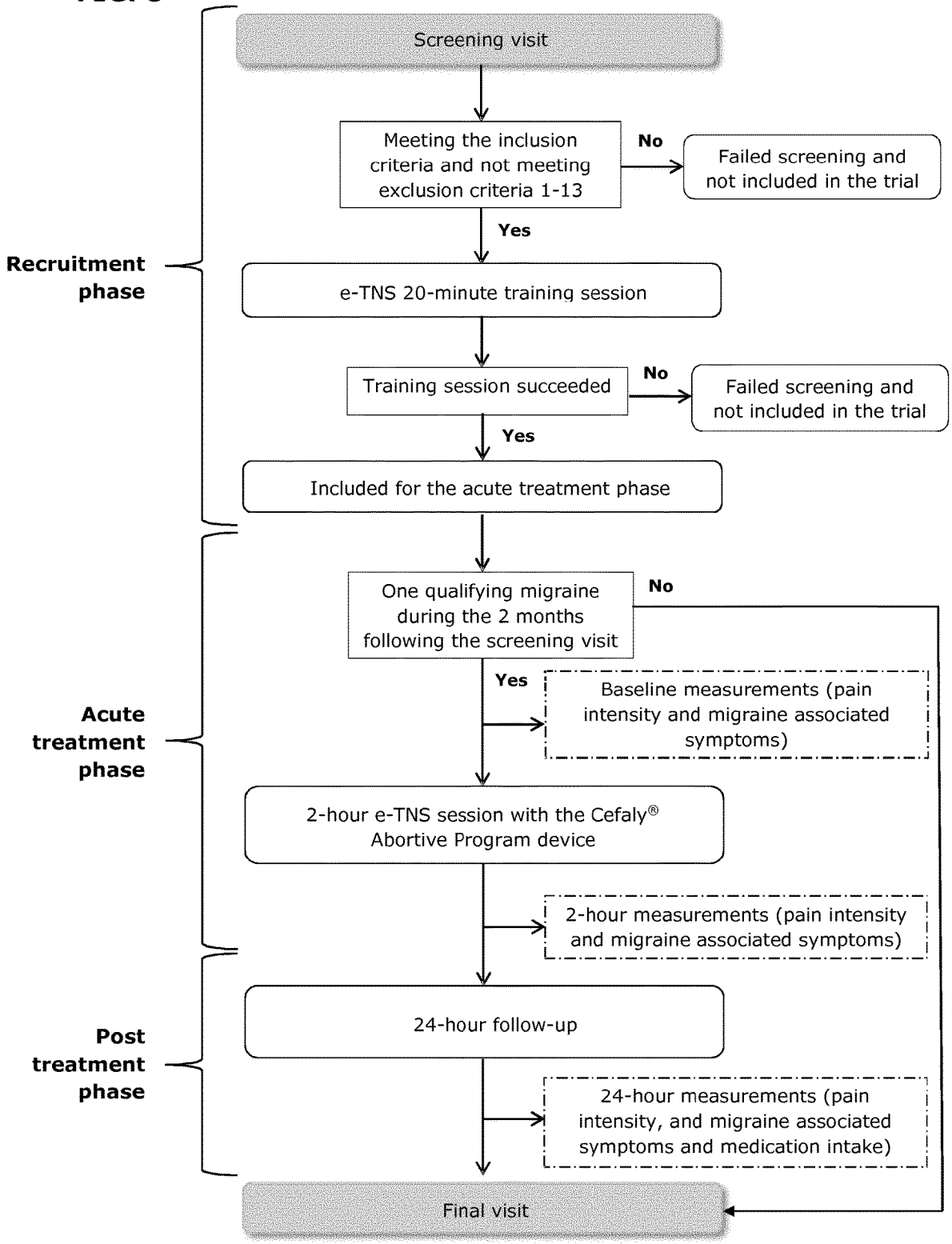
FIG. 8 shows an overview of a clinical trial assessing the efficacy and safety of home use of a treatment system according to the present invention.

An overview of the study protocol is shown in FIG. 8. A total of 60 patients were screened. Patients were trained about the practical use of the treatment system (oral explanation, video, and instruction sheet) and performed themselves a first 20-minute treatment session to check the ability to use the treatment system appropriately. A total of 59 patients were included in the study, as one patient failed the training test (exclusion criterion 14).

Screened patients meeting all inclusion criteria and none of the exclusion criteria were enrolled in the trial and received the treatment system to be used at home to treat a single migraine attack as well as a diary and adverse effects form. The investigator explained to the patient how to fill in these documents.

The patient completed a practice diary for a simulated migraine during the screening visit, to ensure that the patient comprehends the procedure. The investigator or study coordinator then reviewed the diary in detail with the patient.

4.4.2 Acute Treatment Phase

During the 2 months following the screening visit, the patient was instructed to treat a single qualifying migraine headache. A migraine headache is qualifying if all the following conditions are met:
1. The migraine headache severity is moderate or severe (Grade 2 or 3).
2. The migraine headache is associated with at least one of these migraine-associated symptoms: photophobia, phonophobia, nausea, vomiting.
3. The migraine headache started less than four hours ago or the patient woke up with migraine.
4. No other migraine headache or headache has occurred in the previous 48 hours.
5. The migraine headache is not already resolving on its own i.e. the pain is not already diminishing.
6. No acute anti-migraine medication has been taken since the beginning of the migraine headache.

In case of a qualifying migraine headache, the patient had to apply the system for a complete treatment session of 2 hours as soon as the migraine headache was moderate or severe (Grade 2 or 3).

In the diary, the patient noted the grade of the headache pain severity. The patient noted as well the migraine associated symptoms (photophobia, phonophobia, nausea, vomiting) and specified which associated symptom was the most bothersome symptom (MBS). The patient noted this data just before the start of the treatment and 2 hours after the beginning of the treatment session (normally just after removing the device and the electrode if the session ran correctly) (2-hour data), whatever the duration of the stimulation session. The patient also had to record if any aura was associated with the qualifying migraine attack. The patient noted as well the migraine associated symptoms.

Patients were instructed to not take any acute anti-migraine medication during the 2-hour acute treatment phase. Medication intake during the 2-hour treatment phase was considered as a protocol violation.

During the acute treatment phase, when the treatment system was stopped, it was not allowed to be restarted. Duration, intensity and/or interruption were recorded for each patient thanks to a built-in electronic system in the power-providing device.

In the adverse effects form, the patient recorded any adverse effects occurring during the treatment phase. The patients had furthermore been instructed to notify the investigator immediately for any serious or severe adverse experience with the stimulation.

4.4.3 Post-Treatment Phase

Two hours after the beginning of the treatment session, the patient was allowed to take rescue medication if the migraine headache pain was still moderate or severe, or if after initial pain relief (no headache or mild headache pain) a moderate or severe headache was resuming.

The patient had to note the headache pain severity in the diary at 24 hours after the beginning of the treatment session (24-hour data), as well as the migraine associated symptoms. Patients were also instructed to record in their diary the rescue medication intake, if any, during the 24 hours following the beginning of the treatment session.

In the adverse effects form, the patient recorded any adverse effects occurring during the 24 hours following the beginning of the treatment session. The patients had furthermore been instructed to notify the investigator immediately for any serious or severe adverse experience with the stimulation.

4.4.4 Final Visit

The patient were instructed to return to the study site within approximately 4 days after the treatment session to return the treatment system, the diary, and the adverse effects form. The investigator reviewed the paper diary in detail to ensure data accuracy (to avoid any missing data, unclear data or discrepancies).

All adverse effects reported on the adverse effects form have been reviewed by the investigator to assess severity. Additionally, the investigator has inquired for adverse effects not reported on the form.

4.4.5 Patients Compliant with the Study Protocol 11 of the 59 patients were not compliant with the study protocol:
- 4 patients withdrew from the study;
- 1 patient gave no news and did not come back; and
- 6 patients violated the protocol:
  - 2 patients did not experience a qualifying migraine during the 2-month period;
  - 2 patients took rescue medication within the 2-hour treatment period, and one of them also did not report the headache severity or symptoms at 2 hours;
  - 2 patients did not report headache severity or symptoms at 2 hours.

A total of 48 patients completed the study and were eligible for inclusion in the modified intention-to-treat (mITT) analysis.

The pain intensity at baseline was moderate for 68.75% of patients and severe for 31.25% of patients.

A total of 15 patients (31.25%) experienced a migraine attack with aura, while 33 patients (68.75%) experienced a migraine attack without aura.

The most reported MBS at baseline was photophobia (56.25%). Nausea and phonophobia were the second most reported MBS at baseline (22.92% and 18.75%, respectively). Only one patient (2.08%) reported vomiting as the MBS at baseline.

4.5 Statistical Analysis

4.5.1 Hypotheses

1. The treatment allows to achieve pain freedom, as measured by pain freedom at 2 hours and sustained pain freedom at 24 hours.
2. The treatment allows to achieve migraine-associated symptom freedom, as measured by MBS freedom at 2 hours and percentage of patients with absence of migraine-associated symptoms at 2 hours.
3. The treatment allows to achieve pain relief, as measured by pain relief at 2 hours.
4. The treatment allows to reduce the use of rescue medication, as measured by the use of rescue medication between 2 and 24 hours.
5. No serious adverse effects due to 2-hour e-TNS session with the treatment system within the 24 hours following the beginning of the treatment.

4.5.2 Methods of Statistical Analysis

The statistical analysis was executed on a modified intention-to-treat (mITT) basis. Patient data were included in the mITT analysis if all the following conditions are met:
1. The patient treated a qualifying migraine.
2. The patient applied the treatment during at least one minute. (If the patient stopped the 2-hour treatment session before its end for any reason, he/she was kept in the mITT analysis if all the other conditions are met.)
3. The headache pain severity score AND the migraine associated symptom(s) at baseline were reported in the diary.
4. The headache pain severity score OR the migraine associated symptom(s) at 2 hours were reported in the diary.

If the patient took rescue medication between 2 hours and 24 hours after the beginning of the e-TNS session, the headache pain intensity and associated symptoms presence can be affected by the medication and the last value carried forward method (2-hour value carried forward method in this case) was applied for the 24-hour time point headache pain severity and migraine associated symptoms.

4.6 Outcomes

A total of 17 patients (35.42%) were pain-free at 2 hours.
A total of 29 patients (60.42%) were MBS-free at 2 hours:
- 5 out of the 11 patients with nausea as MSB at baseline (45.45%) were MBS-free at 2 hours;
- 0 out of the 1 patients with vomiting as MSB at baseline (0.0%) were MBS-free at 2 hours;
- 17 out of the 27 patients with photophobia as MSB at baseline (62.96%) were MBS-free at 2 hours;
- 7 out of the 9 patients with phonophobia as MSB at baseline (77.78%) were MBS-free at 2 hours;

A total of 34 patients (70.83%) achieved pain relief at 2 hours.

A total of 22 patients (45.83%) had no migraine-associated symptom at 2 hours.

Half of the patients took rescue medication after the treatment session.

A total of 12 patients (25.00%) achieved sustained pain freedom at 24 hours.

On average, the patients used the treatment system during 111.23 minutes. A total of 42 patients used the treatment system during the required 120 minutes.

Out of the 59 patients included in the trial, 15 patients reported at least one adverse effect. A total of 21 adverse effects were reported. All reported adverse effects were minor and fully reversible (they resolved without aftereffects). The most reported adverse effects were burning sensation on forehead (7/21) and an itching, tingling, stinging and/or forehead numbness (5/21) sensation on forehead. It should be noted 4 patients discontinued from the study due to adverse effects: 3 patients due to burning sensation on forehead and one patient due to intense tingling sensation inside head. No serious adverse effects were reported in the course of the trial. No adverse treatment system effect was noted in the course of the trial.

4.7 Comparison to Drugs

The present treatment is compared to several drugs:

[A] Adhesive Dermally-Applied Microarray (ADAM) zolmitriptan (3.8 mg), data from Spierings et al., Cephalalgia 38(2), 215-224 (2018), http://dx.doi.org/10.1177/0333102417737765

[B] Lasmiditan (400 mg), data from Färkkilä et al., The Lancet Neurology 11(5), 405-413 (2012), http://dx.doi.org/10.1016/51474-4422(12)70047-9

[C] Sumatriptan Iontophoretic Transdermal System, data from Goldstein et al., Headache: The Journal of Head and Face Pain 52(9), 1402-1410 (2012), http://dx.doi.org/10.1111/j.1526-4610.2012.02198.x

[D] Sumatriptan Nasal powder (AVP-825), data from Cady et al., Headache: The Journal of Head and Face Pain 55(1), 88-100 (2015), http://dx.doi.org/10.1111/head.12472

[E] Transcranial magnetic stimulation**, data from Lipton et al., The Lancet Neurology 9(4), 373-380 (2010), http://dx.doi.org/10.1016/S1474-4422(10)70054-5

[F] Ubrogepant (100 mg), data from Voss et al., Cephalalgia 36(9), 887-898 (2016), http://dx.doi.org/10.1177/0333102416653233

An overview of the comparison is provided in table 3. The table comprises percentages of patients.

TABLE 3

Comparison of the present study to drugs

|  | Present study | [A] | [B] | [C] | [D] | [E] | [F] |
|---|---|---|---|---|---|---|---|
| Pain freedom at 2 h | 35.4% | 41.5% | 28% | 18% | 34% | 39% | 25.5% |
| MBS freedom at 2 h | 60.4% | 68.3% | NA | NA | NA | NA | NA |
| Pain relief at 2 h | 70.8% | 80% | 65% | 52.9% | 68% | 72% | 58.8% |
| Absence of symptoms at 2 h | 45.8% | NA | NA | NA | 19% (1 h) | NA | NA |
| Use of rescue medication between 2 h and 24 h | 50.0% | NA | 42% | 40% | 37% | 48% (48 h) | NA |
| Sustained pain freedom at 24 h | 25.0% | 31.7% | NA | NA | 28% | 29% | 21.6% |
| Nausea freedom at 2h* | 72.9% | 81.7% | ~26% | 83.6% | NA | 63%*** | 70.6% |
| Vomiting freedom at 2 h* | 95.8% | NA | ~5% | NA | NA | NA | NA |
| Photophobia freedom at 2 h* | 62.5% | 69.5% | ~38% | 51% | NA | 37%*** | 54.9% |
| Phonophobia freedom at 2 h* | 68.8% | 69.5% | ~30% | 55% | NA | 47%*** | 60.8% |
| At least one treatment-emergent adverse effect | 25.4% (18.6%) | 51.8% | 84% | 50% | NA | 14%**** | 29.4% |

*Irrespective of MBS.
**75% of patients had no pain or mild pain at baseline.
***Values from per-protocol data set limited to patients with moderate or severe pain at baseline, while other values are from mITT data set.
****5% for treatment-related adverse effects The present treatment system allows to achieve pain freedom, as measured by pain freedom at 2 hours. Results are better than those reported for other acute treatments, except ADAM zolmitriptan and transcranial magnetic stimulation. Sustained pain freedom at 24 hours associated with the present treatment system is limited due to the high percentage of rescue medication intake, but is within the range reported for other acute treatments (20-30%).

The present treatment system allows to achieve migraine-associated symptom freedom, as measured by MBS freedom at 2 hours and percentage of patients with absence of migraine-associated symptoms at 2 hours. Results are better than those reported for other acute treatments, except ADAM zolmitriptan.

The present treatment system allows to achieve pain relief, as measured by pain relief at 2 hours. Results are better than those reported for other acute treatments, except ADAM zolmitriptan and transcranial magnetic stimulation.

The present treatment system is associated with higher rate of rescue medication intake between 2 and 24 hours than triptans, but is similar to the rate reported for transcranial magnetic stimulation.

In terms of safety, the present treatment system is associated with a highly better safety level than triptans. Compared to ADAM zolmitriptan, that is the triptan with best efficacy results, the number of patients with at least one adverse effect is significantly lower for the present treatment system (18.6%, compared to 51.8% for ADAM zolmitriptan).

Based on these findings, the present treatment system seems to have the better efficacy/safety ratio among the currently available abortive treatments of migraine. Knowing that many patients tend to overuse acute anti-migraine medications, which is a major factor of migraine chronification, this safe and efficient non-drug and non-invasive acute anti-migraine treatment will be a progress for the management of migraine patients.

In an embodiment, the treatment system, the bipolar self-adhesive electrode and/or the power-providing device may be marketed under the registered trademarks Cefaly®, Cefaly® Acute, and/or Cefaly® Abortive Program.

The invention claimed is:

1. A system for the acute non-invasive treatment of a migraine attack of a patient, the system comprising:
   at least one skin electrode configured for placement on a forehead of the patient,
   wherein the system is configured to provide consecutive biphasic electrical pulses via the at least one skin electrode for a prolonged time span, the prolonged time span is at least 10 minutes, wherein the system is configured for providing the consecutive biphasic electrical pulses at a frequency of at least 60 Hz and at most 300 Hz, each of the consecutive biphasic electrical pulses comprises a width of at least 30 microseconds and at most 1000 microseconds, and
   wherein the system is configured for linearly increasing the amplitude of the consecutive biphasic electrical pulses during a first portion of the time span up to a preconfigured upper amplitude that is maintained during a second subsequent portion of the time span, the preconfigured upper amplitude is at least 1 mA and at most 50 mA.

2. The system of claim 1, wherein the biphasic electrical pulses are approximately rectangular biphasic symmetrical pulses with a zero electrical mean.

3. The system of claim 1, wherein the time span is at least 25 minutes.

4. The system of claim 1, wherein the time span is at least 45 minutes.

5. The system of claim 1, wherein the system is configured to provide the consecutive biphasic electrical pulses at a frequency of at least 80 Hz and at most 300 Hz.

6. The system of claim 1, wherein the system is configured to provide the consecutive biphasic electrical pulses at a frequency of about 100 Hz, wherein about encompasses variations of +/−20% or less of and from the specified value.

7. The system of claim 1, wherein each of the consecutive biphasic electrical pulses comprises a width of about 250 microseconds wherein about encompass variations of +/−20% or less of and from the specified value.

8. The system of claim 1, wherein the preconfigured upper amplitude is at least 6 mA and at most 50 mA.

9. The system of claim 1, wherein the preconfigured upper amplitude is about 16 mA, wherein about encompass variations of +/−20% or less of and from the specified value.

10. The system of claim 1, wherein the first portion of the time span is at least 1 minute and at most 30 minutes.

11. The system of claim 1, wherein the first portion of the time span is about 14 minutes, wherein about encompasses variations of +/−20% or less of and from the specified value.

12. The system of claim 1, wherein the linear amplitude increase during the first portion of the time span comprises a slope of at least 1.6 µA/s and at most 833 µA/s.

13. The system of claim 1, wherein the linear amplitude increase during the first portion of the time span comprises a slope of at least 8 µA/s and at most 83 µA/s.

14. The system of claim 1 further comprising a patient-pushable button, wherein, upon pushing the button during the time span, the system is configured to maintain the provided biphasic pulse amplitude at or prior to the time of the pushing of the button throughout the remainder of the time span.

15. The system of claim 1, wherein the at least one skin electrode comprises a bipolar self-adhesive electrode.

16. The system of claim 1, wherein the at least one skin electrode is configured to stimulate the supratrochlear and supraorbital nerves of the ophthalmic branch of the trigeminal nerve of the patient, and wherein the system is configured for transcutaneous transmission of consecutive biphasic electrical pulses via the at least one skin electrode to the supratrochlear and supraorbital nerves of the ophthalmic branch of the trigeminal nerve of the patient for the prolonged time span.

17. The system of claim 1 further comprising a power-providing device configured to receive at least one battery, the power-providing device having two metallic contacts that are positioned in electrical contact with the at least one skin electrode, and wherein the power-providing device is configured to be placed in stable contact with the at least one skin electrode such that the system with the power-providing device and the at least one skin electrode is portable.

18. A method for the acute non-invasive treatment of a migraine attack of a patient, the method comprising:
transcutaneously transmitting consecutive biphasic electrical pulses to the supratrochlear and supraorbital nerves of the ophthalmic branch of the trigeminal nerve of the patient, the consecutive biphasic electrical pulses having a frequency of at least 10 Hz and at most 300 Hz, each of the consecutive biphasic electrical pulses having a width of at least 30 microseconds and at most 1000 microseconds, the consecutive biphasic electrical pulses having a prolonged time span of at least 10 minutes, the consecutive biphasic electrical pulses having a linear amplitude increase during a first portion of the time span up to a preconfigured upper amplitude that is maintained during a second subsequent portion of the time span, and the preconfigured upper amplitude is at least 1 mA and at most 50 mA.

19. The method of claim 18 further comprising:
placing at least one skin electrode on a forehead of the patient, wherein the at least one skin electrode comprises a bipolar self-adhesive electrode; and
providing the consecutive biphasic electrical pulses via the at least one skin electrode to the supratrochlear and the supraorbital nerves for the prolonged time span.

\* \* \* \* \*